(12) United States Patent
Goletz et al.

(10) Patent No.: US 8,609,370 B2
(45) Date of Patent: Dec. 17, 2013

(54) HIGHLY ACTIVE GLYCOPROTEINS-PROCESS CONDITIONS AND AN EFFICIENT METHOD FOR THEIR PRODUCTION

(75) Inventors: Steffen Goletz, Glienicke-Nordbahn (DE); Hans Baumeister, Berlin (DE); Ute Schoeber, Berlin (DE)

(73) Assignee: Glycotope GmbH, Berlin (DE)

( * ) Notice: Subject to any disclaimer, the term of this patent is extended or adjusted under 35 U.S.C. 154(b) by 921 days.

(21) Appl. No.: 10/589,447

(22) PCT Filed: Feb. 14, 2005

(86) PCT No.: PCT/EP2005/001593
§ 371 (c)(1),
(2), (4) Date: Feb. 7, 2008

(87) PCT Pub. No.: WO2005/080585
PCT Pub. Date: Sep. 1, 2005

(65) Prior Publication Data
US 2008/0226681 A1    Sep. 18, 2008

(30) Foreign Application Priority Data

Feb. 13, 2004 (EP) .................................. 04090047
Feb. 19, 2004 (EP) .................................. 04090059
Mar. 11, 2004 (EP) .................................. 04090101

(51) Int. Cl.
*C12N 15/09* (2006.01)
*C12P 21/06* (2006.01)
*C12P 19/00* (2006.01)
*A61K 38/16* (2006.01)

(52) U.S. Cl.
USPC ............ 435/69.1; 435/70.1; 435/72; 530/350

(58) Field of Classification Search
None
See application file for complete search history.

(56) References Cited

U.S. PATENT DOCUMENTS 5,547,933 A * 8/1996 Lin ................................ 514/7.7
7,595,192 B2 * 9/2009 Goletz et al. .................. 435/325

FOREIGN PATENT DOCUMENTS

WO    WO 00/52135    *   9/2000
WO    WO 03/016329 A    2/2003
WO    2005/017130 A2    2/2005

OTHER PUBLICATIONS

Fukuda et al., J. Biol. Chem. 262: 11952-11957, 1987.*
Bonig et al., Bone Marrow Trans 28: 259-264. 2001.*
Muramatsu et al., J. Biochem. 94:799-810, 1983.*
Foglin et al., Electronic J. of Biotech. 5: 243-250, 2002.*
Sigma-Aldrich catalog, downloaded from internet site on Aug. 4, 2011.*
Oliver T. Keppler et al., "UDP-GicNac 2-Epimerase: A Regulator of Cell Surface", Science, vol. 284, pp. 1372-1376, May 21, 1999.
Yeongjin Hong et al., "Lec3 Chinese Hamster Ovary Mutants Lack UPD-N-acetylglucosamine 2-EPimerase Activity Because of Mutations in the Epimerase Domain of the Gne Gene", J. Biol. Chem, vol. 278, No. 52, pp. 53045-53054, Dec. 26, 2003.
Mantey Lars R., et al. "Efficient Biochemical Engineering of Cellular Sialic Acids Using an Unphysiological Sialic Acid Precursor in Cells Lacking UDP-N-acetylglucosamine 2-epimerase", FEBS Letters, vol. 503, Nr-1, pp. 80-84, (2001).
Viswanathan Karthik et al.; "Engineering sialic acid synthetic ability into insect cells: identifying metabolic bottlenecks and devising strategies to overcome them"; Biochemistry; Dec. 30, 2003; vol. 42, No. 51, pp. 15215-15225.
Jacobs C. L. et al.; "Substrate specificity of the sialic acid biosynthetic pathway"; Biochemistry; Oct. 31, 2001; vol. 40, No. 43, pp. 12864-12874.
Fukida M. et al.; "Structures of novel sialylated O-linked oligosaccharides isolated from human erythrocyte glycophorins"; The Journal of Biological Chemistry; Sep. 5, 1987; vol. 262, No. 25, pp. 11952-11957.
Jones Mark B. et al.; "Characterization of the cellular uptake and metabolic conversion of acetylated N-acetylmannosamine (ManNAc) analogues to sialic acids"; Biotechnology and Bioengineering; Feb. 20, 2004; vol. 85, No. 4, pp. 394-405.
Raska et al; Glycosylation Patterns of HIV-1 gp120 Depend on the Type of Expressing Cells and Affect . . . ; Journal of Biological Chemistry, vol. 285, No. 27, Jul. 2010.

* cited by examiner

*Primary Examiner* — Gyan Chandra
(74) *Attorney, Agent, or Firm* — Norris McLaughlin & Marcus, P.A.

(57) ABSTRACT

The present invention relates to highly active glycoproteins with specific sialylation degrees, a pharmaceutical composition for use in diagnosis or therapy comprising the glycoproteins, a method for the determination of highly active glycoproteins and of the conditions for their production, a method for producing the highly active glycoproteins, and a method for differential sialylation of secretory glycoproteins. The invention also relates to the use of the recombinantly expressed highly active glycoproteins for biological purposes and for prophylactic and/or therapeutic treatment or diagnosis of diseases, particularly bone marrow transplantation, neutropenia, cytopenia, AML and myelodysplastic syndromes, cancer, HIV and/or diseases of hematopoietic systems.

10 Claims, 15 Drawing Sheets

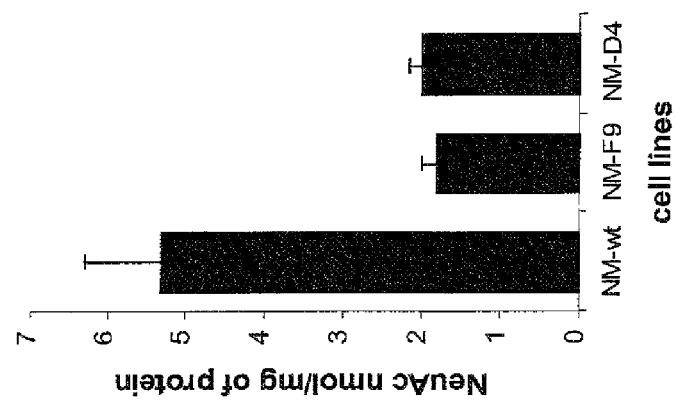
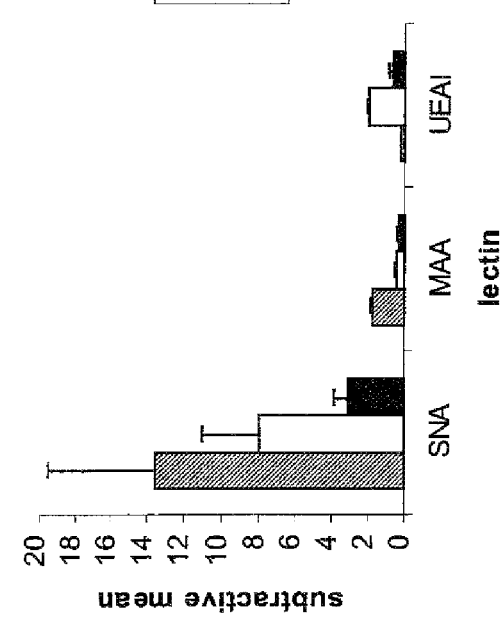
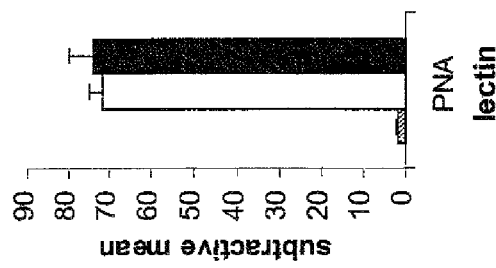
FIG. 3A
FIG. 3B
FIG. 3C

SEQUENCE LISTING

```
<160> NUMBER OF SEQ ID NOS: 19

<210> SEQ ID NO 1
<211> LENGTH: 17
<212> TYPE: PRT
<213> ORGANISM: Artificial
<220> FEATURE:
<223> OTHER INFORMATION: signal peptide of GM-CSF
```

<400> SEQUENCE: 1

Met Trp Leu Gln Ser Leu Leu Leu Leu Gly Thr Val Ala Cys Ser Ile
1               5                   10                  15

Ser

<210> SEQ ID NO 2
<211> LENGTH: 21
<212> TYPE: PRT
<213> ORGANISM: Artificial
<220> FEATURE:
<223> OTHER INFORMATION: signal peptide of T cell receptor

<400> SEQUENCE: 2

Met Ala Cys Pro Gly Phe Leu Trp Ala Leu Val Ile Ser Thr Cys Leu
1               5                   10                  15

Glu Phe Ser Met Ala
            20

<210> SEQ ID NO 3
<211> LENGTH: 22
<212> TYPE: PRT
<213> ORGANISM: Artificial
<220> FEATURE:
<223> OTHER INFORMATION: signal peptide of antibody k light chain

<400> SEQUENCE: 3

Met Glu Thr Asp Thr Leu Leu Leu Trp Val Leu Leu Leu Trp Val Pro
1               5                   10                  15

Pro Gly Ser Thr Gly Asp
            20

<210> SEQ ID NO 4
<211> LENGTH: 19
<212> TYPE: DNA
<213> ORGANISM: Artificial
<220> FEATURE:
<223> OTHER INFORMATION: forward primer beta-actin

<400> SEQUENCE: 4
ggcatcgtga tggactccg                                              19

<210> SEQ ID NO 5
<211> LENGTH: 19
<212> TYPE: DNA
<213> ORGANISM: Artificial
<220> FEATURE:
<223> OTHER INFORMATION: reverse primer beta-actin

<400> SEQUENCE: 5
gctggaaggt ggacagcga                                              19

<210> SEQ ID NO 6
<211> LENGTH: 21
<212> TYPE: DNA
<213> ORGANISM: Artificial
<220> FEATURE:
<223> OTHER INFORMATION: forward primer C1GalT1

<400> SEQUENCE: 6
gagattccag agataccatt g                                           21

<210> SEQ ID NO 7
<211> LENGTH: 20
<212> TYPE: DNA

<213> ORGANISM: Artificial
<220> FEATURE:
<223> OTHER INFORMATION: reverse primer C1GalT1

<400> SEQUENCE: 7
cgttcaggta aggtaggttg                                           20

<210> SEQ ID NO 8
<211> LENGTH: 30
<212> TYPE: DNA
<213> ORGANISM: Artificial
<220> FEATURE:
<223> OTHER INFORMATION: forward primer C2GNT

<400> SEQUENCE: 8
gtgctcagaa tggggcagga tgtcacctgg                                 30

<210> SEQ ID NO 9
<211> LENGTH: 30
<212> TYPE: DNA
<213> ORGANISM: Artificial
<220> FEATURE:
<223> OTHER INFORMATION: reverse primer C2GNT

<400> SEQUENCE: 9
tcactactag gattctcccc agcaagctcc                                 30

<210> SEQ ID NO 10
<211> LENGTH: 20
<212> TYPE: DNA
<213> ORGANISM: Artificial
<220> FEATURE:
<223> OTHER INFORMATION: forward primer ST3Gal-I

<400> SEQUENCE: 10
atgaggtgga cttgtacggc                                            20

<210> SEQ ID NO 11
<211> LENGTH: 18
<212> TYPE: DNA
<213> ORGANISM: Artificial
<220> FEATURE:
<223> OTHER INFORMATION: reverse primer ST3Gal-I

<400> SEQUENCE: 11
aacggctcca gcaagatg                                              18

<210> SEQ ID NO 12
<211> LENGTH: 20
<212> TYPE: DNA
<213> ORGANISM: Artificial
<220> FEATURE:
<223> OTHER INFORMATION: forward primer ST3Gal-II

<400> SEQUENCE: 12
ccctgctctt cacctactcg                                            20

<210> SEQ ID NO 13
<211> LENGTH: 19
<212> TYPE: DNA
<213> ORGANISM: Artificial
<220> FEATURE:
<223> OTHER INFORMATION: reverse primer ST3Gal-II

<400> SEQUENCE: 13
gcatcatcca ccacctctg                                             19

```
<210> SEQ ID NO 14
<211> LENGTH: 22
<212> TYPE: DNA
<213> ORGANISM: Artificial
<220> FEATURE:
<223> OTHER INFORMATION: forward primer ST6Gal-I

<400> SEQUENCE: 14
aaaaacctta tccctaggct gc                                      22

<210> SEQ ID NO 15
<211> LENGTH: 20
<212> TYPE: DNA
<213> ORGANISM: Artificial
<220> FEATURE:
<223> OTHER INFORMATION: reverse primer ST6Gal-I

<400> SEQUENCE: 15
tggtagtttt tgtgcccaca                                         20

<210> SEQ ID NO 16
<211> LENGTH: 18
<212> TYPE: DNA
<213> ORGANISM: Artificial
<220> FEATURE:
<223> OTHER INFORMATION: forward primer ST6GalNAc-I

<400> SEQUENCE: 16
accacagcca agacgctc                                           18

<210> SEQ ID NO 17
<211> LENGTH: 20
<212> TYPE: DNA
<213> ORGANISM: Artificial
<220> FEATURE:
<223> OTHER INFORMATION: reverse primer ST6GalNAc-I

<400> SEQUENCE: 17
aagggtggtg caaagtgttc                                         20

<210> SEQ ID NO 18
<211> LENGTH: 21
<212> TYPE: DNA
<213> ORGANISM: Artificial
<220> FEATURE:
<223> OTHER INFORMATION: forward primer ST6GalNAc-II

<400> SEQUENCE: 18
ctgccagtaa attcaagctg c                                       21

<210> SEQ ID NO 19
<211> LENGTH: 22
<212> TYPE: DNA
<213> ORGANISM: Artificial
<220> FEATURE:
<223> OTHER INFORMATION: reverse primer ST6GalNAc-II

<400> SEQUENCE: 19
ttgcttgtga tgaatccata gg                                      22
```

HIGHLY ACTIVE GLYCOPROTEINS-PROCESS CONDITIONS AND AN EFFICIENT METHOD FOR THEIR PRODUCTION

The present invention relates to highly active glycoproteins with optimized sialylation degrees, a pharmaceutical composition for use in diagnosis or therapy comprising the glycoproteins, a method for the determination of highly active glycoproteins and of the conditions for their production, a method for producing the highly active glycoproteins, and a method for differential sialylation of secretory glycoproteins. The invention also relates to the use of the recombinantly expressed highly active glycoproteins for biological purposes and for prophylactic and/or therapeutic treatment or diagnosis of diseases, particularly bone marrow transplantation, neutropenia, cytopenia, AML and myelodysplastic syndromes, cancer, HIV and/or diseases of hematopoietic systems.

Glycoproteins are a diverse group of which the function and occurrence vary widely among each other. Among the proteins of therapeutic potential most proteins are glycosylated, such as many hormones (e.g. Growth hormone, Glycagon, FSH and LH), growth factors (e.g. GM-CSF, G-CSF, VEGF and Erythropoietin), cytokines (e.g. IL-2, IL-7, Interferon-alpha and -beta, TNF-alpha), anti-coagulantia (e.g. Lepirudin, Desirudin), blood clotting factors (e.g. factors VII, VIII and IX), vaccines (e.g. Hepatitis B antigen) and antibodies. To produce such proteins the established cellular production systems are unable to produce proteins with the original human glycosylation. Prokaryotic (e.g. bacteria) and most eukaryotic cell systems (e.g. yeast, insect and plant cell) synthesize proteins that lack glycosylation or carry glycans which largely differ from human carbohydrate chains. Chinese hamster ovary (CHO) cells are a commonly used production system that is able to glycosylate proteins in a similar way as human cells do but with some important differences, such as in galactosylation, fucosylation, particular glycosylation with N-acetylglycosamines, and especially in various aspects of sialylation.

At the time when these production systems were established it was sufficient to produce therapeutic proteins that were at least to some degree active. Today large efforts concentrate to improve the activity of a therapeutic protein with the aim (i) to reduce the number and concentration of the applied doses of the therapeutic proteins, (ii) to reduce the costs of a therapy, and (iii) to reduce the side effects.

One strategy is to increase the productivity of the expression system which, however, in most cases result in no or only very aberrant glycosylation which is in most cases not relevant for the protein. Other problems arise for example with decreased stability and folding of the molecules often resulting in the necessity of additional steps in the production which are time and cost consuming and result in losses, side effects, and suboptimal bioactivities.

The major strategy to improve the bioactivity of proteins is to elongate their serum-half life and hence their bioavailability. This can be done by the process called PEGylation where certain forms of polyethyleneglycol is added chemically to the produced protein. PEG increases the molecular weight and hence the serum half-life. However, several problems are associated with this process, for example, in nearly all cases PEGylation decreases the activity of a protein by its cellular effector function, repetitive administration in humans often results in an adverse immune response as neutralizing antibodies, and/or the production process needs additional chemical modification resulting in a multistep process with additional costs, losses and time.

Also the modification of the carbohydrate chains is in the focus in order to improve the serum-half life of recombinantly expressed proteins. The technologies thereby focus on the maximization of the sialylation degree of a recombinant glycoprotein. Sialic acids are the most prevalent terminal monosaccharides on the surface of eukaryotic cells and it is generally believed that the more a glycoprotein is sialylated the longer is its serum half-life during circulation. This is based on the presence of certain receptors as the asialoprotein-receptor in the liver which binds circulating non-sialylated proteins and directs them into the cell for degradation.

Several strategies have been proposed to increase the sialylation degree to the highest possible degree of sialylation of recombinant glycoproteins including (i) production of recombinant host cell lines that overexpress particular sialyltransferases or galactosyltransferases which are responsible for providing most terminals for sialylation, (ii) prevention of host cell sialic acid degradation by regulating glycohydrolytic enzymes, e.g. by adding of Cu ions into the medium, (iii) culture of recombinant glycoprotein producing host cells in the presence of additional sugar conjugates and other substrates for increasing the oligosaccharide production, (iv) variation of culture conditions, (v) mutation of the protein for introduction of additional carbohydrate chains and hence more sialic acids, (vi) and complete in vitro sialylation with purified sialyltransferases after production of the glycoprotein. All these technologies are connected with series of disadvantages and are only designed for the increase of the serum half-life by maximizing the sialylation degree.

The prior art has, as mentioned before, a series of critical disadvantages and addresses only a small fraction of the potential of glycosylation for improvement of bioactivities, decrease of side effect, or toxicities, and hence can not deliver glycoproteins for certain applications. The prior art lacks almost any knowledge whether the biological activity of a glycoprotein correlates with the degree of sialylation, because there is just no available suitable test and production system for corresponding recombinant glycoproteins.

The present invention solves this problem by providing a highly active glycoprotein produced by a process comprising expression of said highly active glycoprotein in an expression cell line, harboring at least one defect in the sugar nucleotide biosynthetic pathway of sialic acids and which is transfected with nucleic acid encoding the glycoprotein, in a medium supplemented with a concentration of at least one sialic acid precursor additive, the concentration being determined by a process comprising:

(i) expression of a plurality of different sialylation forms of said glycoprotein by differential sialylation using different concentrations of at least one sialic acid precursor; and (ii) determination of the activity of the different sialylation forms in comparison with a reference glycoprotein in (a) suitable bioassay(s); and (iii) selection of the sialylation form with the higher/highest activity and determination of the concentration of the sialic acid precursor additive(s) which is correlated with the higher/highest activity level of said glycoprotein.

Therefore, the present invention also relates to a process.

According to the present invention the term "reference glycoprotein" mean a glycoprotein with the same or a similar protein sequence like the inventive glycoprotein, preferably those with the same protein sequence. A lack of the glycosylation structure is possible as well. The reference glycoprotein possesses a defined activity and can be of natural origin or recombinantly expressed. Preferred references are the known recombinant glycoproteins. In case of mutations of a particular protein sequence of prior art, resulting in an improved activity, for example for receptor mediated activity in vitro, the higher active glycoprotein of the present invention can be higher active in this respect and/or in respect to another bioactivity, such as immunogenicity, without being better in the aforementioned activity. In these examples the higher activity in the immunogenicity is advantageous for use in mammals, preferably humans, and therefore equals a higher active glycoprotein in sense of the invention. A person skilled in the art is able to select appropriate selection criteria in respect to pre-clinical and/or clinical test regimens.

According to the present invention the term "expression cell line" means a cell or a cell line which can be used for the expression of proteins, glycoproteins, viruses or other biologic material, with or without further recombinant expression of a target gene or infection with viruses or suitable material known to those skilled in the art by technologies known to those skilled in the art or described elsewhere in this invention.

According to the present invention the term "expression cell line harboring at least one defect in the sugar nucleotide biosynthetic pathway of sialic acids" means an expression cell line which a defect in an enzyme involved in the synthesis of the CMP-sialic acid. Defect means that the according enzymatic activity is decreased or completely absent and can be due to different primary defects for example on the level of the gene of the enzyme, the expression of the gene, the activity of the enzyme, or the bioavailability of the enzyme relevant for its function. Enzymes are for example UDP-N-acetylglucosamine-2-epimerase, kinase (e.g. N-acetylmannosamine kinase, N-acetylglucosamine kinase), N-acetylneuraminic acid-9-P (Neu5Ac-9-P)-synthetase, Neu5Ac-9-P-phosphatase and CMP-Neu5Ac synthetase. More preferred defect in the sugar nucleotide biosynthetic pathway of sialic acids is a mutation of an epimerase and even more preferred is a defect in the UDP-N-acetylglucosamine-2-epimerase resulting in the lack of its mRNA expression.

The defect results in a decreased sialylation or a nearly complete or complete absence of sialylation of the cells under standard conditions and/or under serum free conditions. This decreased sialylation can be partially or completely reconstituted by addition of sialic acid precursor additives. This defect is not restricted to defects in one or more enzymes involved in the synthesis of the CMP-sialic acid but can also be in other enzymes provided the effect can be partially or completely reconstituted by addition of sialic acid precursor additives. One example herefore, however not the only one, are the according sugar transporting enzymes as the CMP-sialic acid transporter. Those skilled in the art are able to determine which single defect or combination of defects are suitable in relevance to the invention, some of those are described in more detail below.

According to the present invention the term "transfection" means methods known to those skilled in the art which can be used for the delivery of genetic material into cells for the expression of recombinant proteins by viral infection or transfection methods including but not restricted to calcium phosphate coprecipitation, electroporation, complex formation with DEAE-dextran or cationic lipid reagents and microinjection thereby introducing nucleic acid into the cell of the expression cell line.

According to the present invention the term "nucleic acid encoding the glycoprotein" means nucleic acid sequences encoding a mammalian glycoprotein of interest or active fragments and/or mutants thereof whereby any glycoprotein can be used, preferably any glycoprotein of human origin. Examples of mammalian glycoproteins include molecules such as cytokines and their receptors, for instance the tumor necrosis factors TNF-alpha and TNF-beta; renin; human growth hormone and bovine growth hormone; growth hormone releasing factor; parathyroid hormone; thyroid stimulating hormone; lipoproteins; alpha-1-antitrypsin; insulin A-chain and B-chain; gonadotrophins, e.g. follicle stimulating hormone (FSH), luteinizing hormone (LH), thyrotrophin, and human chorionic gonadotrophin (hCG); calcitonin; glucagon; clotting factors such as factor VIIIC, factor IX, factor VII, tissue factor and von Willebrands factor; anti-clotting factors such as protein C; atrial natriuretic factor; lung surfactant; plasminogen activators, such as urokinase, human urine and tissue-type plasminogen activator; bombesin; thrombin; hemopoietic growth factor; enkephalinase; human macrophage inflammatory protein; a serum albumin such as human serum albumin; mullerian-inhibiting substance; relaxin A-chain and B-chain; prorelaxin; mouse gonadotropin-associated peptide; vascular endothelial growth factor; receptors for hormones or growth factors; integrin; protein A and D; rheumatoid factors; neurotrophic factors such as bone-derived neurotrophic factor, neurotrophin-3, -4, -5, -6 and nerve growth factor-beta; platelet-derived growth factor; fibroblast growth factors; epidermal growth factor; transforming growth factor such as TGF-alpha and TGF-beta; insulin-like growth factor-I and -II; insulin-like growth factor binding proteins; CD proteins such as CD-3, CD-4, CD-8 and CD-19; erythropoietin (EPO); osteoinductive factors; immunotoxins; a bone morphogenetic protein; an interferon such as interferon-alpha, -beta, and -gamma; colony stimulating factors (CSF's), e.g. M-CSF, GM-CSF and G-CSF; interleukins (IL's), e.g. IL-1 to IL-12; superoxide dismutase; T-cell receptors; surface membrane proteins; decay accelerating factor; antibodies and immunoadhesins; Glycophorin A; MUC1.

Preferred glycoproteins are selected from the group comprising Glycophorin A, EPO, G-CSF, GM-CSF, FSH, hCG, LH, interferons, interleukins, antibodies and/or fragments thereof.

According to the present invention the term "glycoprotein" is also defined as a virus, a virus particle, or a viral protein.

In a preferred embodiment of the invention the nucleic acid encodes a secretory form of the glycoprotein or a fragment hereof. In a preferred embodiment the secretory form lacks transmembrane domains. In a further preferred embodiment the nucleic acid encoding the secretory form comprises at least one secretory signal. In a most preferred embodiment the secretory signal is from GM-CSF. Further embodiments and details are described in more detail below.

According to the present invention the term "sialic acid precursor additive" means any natural or synthetic compound able to reconstitute partially or completely the defect in the sugar nucleotide biosynthetic pathway of sialic acids resulting in a partial or complete sialylation of the glycoprotein. In a preferred embodiment of the invention the addition of different concentrations of the sialic acid precursor additive results in a series of different sialylation forms of the glycoprotein with different sialylation degrees. Thereby a sialylation form of the glycoprotein can be composed of a single glycoform or of a group of glycoforms. This can be achieved either by using a single sialic acid precursor additive or by using a combination of two or more precursor additives. In a preferred embodiment of the invention a sialic acid intermediate and/or a glycoprotein carrying sialic acid is used as a sialic acid precursor additive. In a further preferred embodiment the sialic acid precursor additive is ManNAc, acetylated ManNAc, peracetylated ManNAc or fetuin. In a further preferred embodiment a combination of ManNAc, acetylated ManNAc, or peracetylated ManNAc and fetuin is used.

Preferred are sialic acid precursor additives which result in glycoproteins with natural sialic acid modifications. A natural sialic acid modification is such a modification which can be found in organisms as a starting material, an intermediate glycoform or a final glycoform. Further preferred are natural glycoproteins, glycosylation forms, which are as nearly as possible to the glycoforms which exist naturally in the body of the organism the glycoform will be used. For example, a glycoform of a human glycoprotein which has carbohydrate chains with sialic acids which resemble the carbohydrate chains occurring in human or any biological material derived from a human. Those preferred forms do not carry sialic acids that are modified by unnatural side chains not occurring in organisms. For example, the sialic acid incorporated in a glycoprotein or glycolipid does not comprise substituted, deleted, added, prolonged or shortened side chains which could be introduced by chemical synthesis and/or novel interlinkages to the sialic acid which do not occur in organisms.

In the preferred form of the present invention the glycosylation of any cellular product is not changed or modified by chemically engineered precursors or metabolites resulting in non-natural sialic acid modifications but by optimizing the degree of the natural glycosylation, preferentially the sialylation. Chemically modified sialic acid metabolites may only be used in a way that does not affect the natural glycosylation. For example, N-acetylmannosamine (ManNAc) may be replaced as cell culture medium supplement by acetylated ManNAc or peracetylated ManNAc which is taken up by the cell much easier than natural ManNAc. In the cell the additional acetyl-residues are cleaved off and ManNAc is processed for biosynthesis of CMP-sialic acid. Therefore, glycoproteins produced by cells that were treated with acetylated ManNAc do not display any synthetically modified carbohydrates, such as synthetically acetylated sialic acid.

According to the present invention the term "different sialylation form" means a glycoform of the glycoprotein which differs from another glycoform by at least one sialic acid. The difference in the sialic acid can be either in amount of sialic acids and/or in the position of at least one sialic acid on the rest of the molecule. A particular sialylation form can be composed of a single glycoform or of a mixture of several glycoforms of the glycoprotein whereby different sialylation forms differ at least in one glycoform and/or in the relative composition of glycoforms.

The sialylation degree of at least one sialylation form can be determined by biochemical and/or chemical methods known to those skilled in the art. For example, a fast method is to stain cells or glycoproteins with sialic acid specific antibodies or lectins, such as SNA and MAA, or with antibodies or lectins that recognize the sialic acid-free glycan, such as the antibodies A78-G/A7 and Nemod-TF1 or the lectin PNA. Stained cells can be analyzed by flow cytometry and stained glycoproteins can be analyzed by a routine ELISA when the glycoprotein is purified or by a sandwich ELISA using a glycoprotein-specific antibody to catch the glycoprotein to be analyzed. All these methods that are known to people skilled in the field of art allow the monitoring of differential sialylation of cells or a glycoprotein, whereby the amount of bound sialic acid specific antibodies or lectins directly correlates with the amount of sialic acids bound to the cell or the glycoprotein, while the amount of bound antibodies or lectins that recognize sialic acid-free glycans inversely correlates with the amount of sialic acids bound to the cell or the glycoprotein. Another method to quantify the sialic acid content is to cleaved off either enzymatically by using a neuraminidase or chemically by acid hydrolysis all sialic acids bound to a glycoprotein. The concentration of sialic acids in the sample is then determined by fluorometric staining of sialic acids with 1,2-diamino-4,5-methylendioxybenzen (DMB) and HPLC analysis using an fluorometric detector. Alternatively, the amount of released sialic acid is quantified by converting the sialic acid in presence of thiobarbiturate and beta-formylpyruvate to a pink dye which can be detected colorimetrically at 549 nm. To get data regarding the number of sialic acids bound to N- or O-glycans, the whole N- or O-glycan is released enzymatically or chemically. There are several methods available to persons skilled in the art to analyze the released glycans with regard to the antennarity (e.g. by HPAEC-PAD), the number of bound sialic acids (e.g. by HPAEC-PAD in combination with anion exchange chromatography), the composition of monosaccharide (e.g. by HPAEC-PAD after acid hydrolysis of glycans) and/or the exact structure (e.g. by mass spectrometry).

In the meaning of the invention, "activity" is a function or set of functions performed by a molecule in a biological context. Generally, glycoproteins produced by the methods of the invention are more active and/or more effective biological products than glycoproteins produced by prior art. The present invention therefore relates to human highly active glycoproteins and their use in diagnosis, therapy or other biological systems and tests comprising said glycoproteins. In the meaning of the invention, the term "highly active glycoprotein", equivalents of the contents and grammatical equivalents thereof are to understood as an improved or optimal activity with regard to the selected application, whereby the activity could be either approximated to a limiting value, for example being minimized or maximized, or set to a medium value representing a higher or lower activity compared to the corresponding glycoprotein produced by prior art and/or to another sialylation form produced by the differential sialylation method of the invention. Improved or higher activity in sense of the invention also means a favorable activity in sense of its biological and/or pharmaceutical meaning. For example, the biological activity of a glycoprotein could be increased to an extend by decreasing adverse biological effects, e.g. by the reduced stimulation of adverse immune effects or a decreased immunogenicity. The methods of the present invention can be effectively used to generate glycoproteins with an optimized serum half-life, pharmacokinetics, stability, antigenicity and/or immunogenicity.

According to the present invention the term "determination of the activity of the different sialylation forms" means determination of the activity in a suitable bioassay which is able to determine the activity of the glycoprotein. Those skilled in the art are able to identify suitable bioassays or to build up suitable bioassays. According to the present invention such bioassays include for example biological in vitro assays, including cellular or molecular or mixed assays, such as proliferation assays, apoptosis assays, cell adhesion assays, signaling assays, migration assays, cell cytotoxicity assays, phagocytosis assays, lysis assays, and binding assays. Such bioassays also include in vivo assays using animal models or humans, such as biodistribution, pharmacokinetic, pharmacodynamic test, serum-half life tests, tests for bioavailability, efficacy test, localization tests, treatment and prophylaxe tests of diseases including clinical studies. Such bioassays also include chemical, physical, physiochemical, biophysical and biochemical tests, such as stability towards temperature, shear stress, pressure, pH, conjugation and others. Such bioassays also include tests for the immunogenicity and/or antigenicity in order to improve the properties of the glycoprotein in respect to its clinical use. Those skilled in the art are able to determine the activity or a combination of described activities of a glycoprotein and its sialylation forms.

In a preferred embodiment the higher activity of the glycoprotein is characterized by a higher activity in at least one in vitro model and/or a higher activity in at least one in vivo model and/or a higher stability and/or a longer serum half-life and/or a longer bioavailability and/or an improved immunogenicity and/or an improved antigenicity determined by at least one bioassay. The improvement in the overall activity which is also called herein higher activity can lead for examples to improvements like lower dosages, longer time intervals for administration, less side effects and no or lower toxicity of the product when used in humans or according organisms resulting in largely improved pharmaceuticals.

According to the present invention the term "selection of the sialylation form with the higher activity" means the selection of the sialylation form of the glycoprotein which has a higher activity compared in at least one of bioassay. This comparison can be done either by comparing at least one sialylation form expressed by a method of the invention with a prior art glycosylation form of the glycoprotein or by comparing at least two sialylation forms expressed by a method of the invention. Preferably the highly active glycoprotein is chosen from more than two different sialylation forms in order to achieve, identify and produce a rather optimized glycoform. Those skilled in the art are able to determine which sialylation form has a higher activity in respect to a particular bioassay. In a preferred embodiment the activities of a combination of bioassays are considered in order to select the sialylation form with the higher activity. Thereby not each bioassays has to show a higher activity but depending on the use and the features of a particular glycoprotein some favorable biological effects can compensate for others which are less favorable and still resulting in a overall higher activity of the glycoform in sense of the invention. For example, a certain glycoform can result in a much higher activity by binding to its receptors to cells thereby triggering secondary effect, such as induction of proliferation, but show a slightly decreased serum-half life. In combination the higher activity triggering the receptor more then compensates for the shorter bioavailability in the overall bioactivity. In another example, a shorter half-life and a higher activity towards the receptor triggering are both advantageous. In yet another example the activity in vivo is not improved but the stability in vitro improves the production and storage of the glycoprotein. In yet another example, a long half-life but a lower activity is needed. Therefore the actual advantageous sialylation form has to be determined on the particular glycoprotein basis in respect to its later use. The present invention enables this for the first time in this integrated system. All this aspects are dependent on the single glycoprotein to be determined which differ to a large degree and can not be predicted and hence shows the necessity of the later described processes of the invention. By using the present invention those skilled in the art are able to select the appropriate bioassay and/or combination of bioassays and the sialylation form of their glycoprotein with higher activity for their desired use of the glycoprotein in above mentioned respects and hence improve the glycoprotein in comparison to glycosylation forms which can be produced by standard procedures. Those skilled in the art are herefrom, by using the present invention, also able to determine the concentration of sialic acid precursor additive or a combination of sialic acid precursor additives which is correlated with the higher activity level of said glycoprotein.

According to the present invention the term that a plurality of different sialylation forms which are expressed by differential sialylation and compared in bioassays can also mean one sialylation form expressed by the processes of the invention which shows a higher activity compared to at least one different sialylation or glycosylation form obtained by prior art when tested in a bioassay.

All definitions and descriptions described above are also valid for the above and below described glycoproteins and processes.

It has been surprisingly found that a recombinantly expressed glycoprotein according to the present invention shows highest biological activity when sialylated to a specific degree corresponding to a special concentration of sialic acid precursor additive. This sialylation degree which correlates with the highest biological activity is different for each glycoprotein that is analyzed, it is not predictable and not necessarily the highest sialylation degree achievable. To identify the inventive sialylation degree of a glycoprotein, cells are used and/or generated that are deficient in the ability to sialylate in a way that the cellular defect allows a reconstitution of the sialylation and the generation of different sialylation degrees. One way to achieve reconstitution of the sialylation is by supplementing the culture medium of said cells with sialic acid precursor additive of the sialic acid biosynthesis pathway. Using said defective cells and at least one sialic acid precursor additive the degree of sialylation of any glycoprotein of the invention produced by said cells can be controlled differentially by changing the amount of said sialic acid precursor additive added to the culture medium. At least two different sialylation forms can be achieved. If using only two different concentrations of aforementioned additives, the concentration gradient has to be favorably large to ensure the generation of different sialylation forms. Preferably a low concentration and a high concentration which maximum is defined by process features, such as viscosity, solubility, aw value, etc. are chosen. At least two forms and preferably multiple forms of differentially sialylated glycoproteins (different sialylation forms) can be isolated and analyzed for their properties, such as glycosylation, preferentially sialylation, activity, serum half-life, pharmacokinetics, pharmacodynamics, in vivo bioactivity, antigenicity and immunogenicity. In that way the optimal sialylation degree of said glycoprotein for its activity or any other property is identified by a single or a combination of criteria as described above, and the conditions for production of that optimally sialylated glycoprotein can be transferred to a production process using said defective cells as production cells.

The invention also teaches a special process for the generation of highly active glycoprotein and the highly active glycoprotein itself. In these special cases, a particular sialylation form can be generated without the need of comparing it with a second form generated by expression in the according expression cell line using a different concentration of sialic acid precursor additive, when the optimized concentration of the sialic acid precursor additive can be determined by other technologies or deduced from logic thinking by those skilled in the art, as for example described in the example below. These special cases are explicitly also falling under the present invention in sense of the highly active glycoprotein as well as for the processes of the invention. In these cases the basic inventory principle of the invention is still the central and critical part of this process and of the obtained highly active glycoprotein. For this see also other description of examples below and above. An example is the GPA with no or minimal sialylation, which is further described below in one of the examples, where the aim can be from the beginning the generation of a form with minimal sialylation and maximal Thomsen-Friedenreich. Therefore it can be sufficient to generate only the form with the minimal sialylation without adding sialic acid precursor additive and preferably without any sialoglycoprotein in the medium. The suitability of this form for further use can be determined by comparing it to at least one other sialylation form but instead of this can be compared to sialylated or less sialylated GPA from human sources instead. Another example are those where a maximum sialylation is known to be wanted where it can be sufficient to use a maximum of sialic acid precursor additive. However, in the latter case it is nearly in all cases advantageous to optimize the maximum sialylation by optimizing the composition and concentration of the sialic acid precursor additives by generating various sialylation forms as described elsewhere in the invention. In this specialized case it might be sufficient to use a technology for determination of the sialic acid degree as a single bioassay, however, the combination with other bioassays is preferred.

The new technology holds a high potential for the generation of new glycoproteins and the improvement of various glycoproteins including the generation of improved biogenerics.

In the following defects in the sugar nucleotide biosynthetic pathway of sialic acids are further described. In the present invention, the highly active glycoprotein is produced by an expression cell line with a defect that results in a diminished cellular capability to sialylate, preferentially a complete loss of the capability to sialylate, and that can be reconstituted allowing a differentially controlled sialylation. The molecular defect of the cell also termed as "defect in the sugar nucleotide biosynthetic pathway of sialic acids" may be a loss-of-function of proteins that are involved in the metabolism of sialic acids, e.g. in the sugar transportation, such as the CMP-sialic acid transporter, or in the biosynthesis of CMP-sialic acids, such as kinases, dehydrogenases, phosphatases, synthetases, transketolases, transaldolases, isomerases, transferases and epimerases. The molecular defect resulting in sialylation incompetent cells with decreased or lacking sialylation may also be a gain-of-function of proteins involved in the metabolism of sialic acids, e.g. of enzymes that cleave off sialic acids from carbohydrates, such as the neuraminidases. Preferred targets are such proteins that are responsible for transportation of the CMP-sialic acid and enzymes catalyzing a rate-limiting step in the sialic acid biosynthesis pathway. More preferably, the defect concerns an epimerase and most preferably the UDP-GlcNAc-2-epimerase.

Prior art teaches that N-acetylmannosamine (ManNAc) plays an important role within the biosynthesis of CMP-sialic acids. ManNAc is formed from UDP-N-acetylglucosamine (UDP-GlcNAc) by the action of UDP-GlcNAc-2-epimerase representing the rate-limiting step in the cellular biosynthesis of sialic acid. ManNAc is then phosphorylated by a specific kinase (e.g. N-acetylmannosamine kinase, N-acetylglucosamine kinase). ManNAc-6-P is condensed with phosphoenolpyruvate to N-acetylneuraminic acid-9-P (NeuAc-9-P) by Neu5Ac-9-P-synthetase, the phosphate is subsequently released by Neu5Ac-9-P-phosphatase, and Neu5Ac is activated by CMP-Neu5Ac synthetase. CMP-Neu5Ac is then transported into the Golgi compartment of the cell by specific transporters (e.g. the CMP-sialic acid transporter) and there it serves as a donor for different sialyltransferases, for example the ST6GlcNAc sialyltransferase, ST6GalNAc-I to VI, ST3Gal-I to VI and ST6Gal-I, that transfer the sialic acid to terminal galactose (Gal)-, N-acetylgalactosamine (GalNAc)- or N-acetylglucosamine (GlcNAc)-residues of glycoproteins or glycolipids.

Each enzyme of the sialic acid biosyntheses, such as the UDP-GlcNAc-2-epimerase, kinase, Neu5Ac-9-P-synthetase, Neu5Ac-9-P-phosphatase and CMP-Neu5Ac synthetase, or each protein necessary for the transport into the Golgi compartment can be influenced to alter, preferably to diminish, and more preferably to completely interrupt the cellular ability to sialylate in a way that the defect can be reconstituted by providing the defective cell with the product of the defective enzyme. The ability of a cell to sialylate can also be affected by changes in the transfer of the sialic acid to carbohydrates catalyzed by sialyltransferases.

There are many options how said cellular defect can arise or be specifically generated targeting protein synthesis and function on the genetic, transcriptional, translational or protein level:

Mutations in the gene encoding a specific protein result often in a loss-of-function of that protein or sometimes in a protein that gains a function. For example, a mutation that creates a stop codon within the coding region of a gene by the substitution of one or two nucleotides or by a frame-shift which could be caused by the introduction or deletion of (1+n) or (2+n) nucleotides, n being a positive integer multiple of 3. There are many other "loss-of-function" and "gain-of-function" gene mutations known to skilled persons. These gene mutations may also affect the transcription of a gene. There are many methods known to skilled persons to induce randomly genetic mutations by chemical mutagens, such as ethyl methanesulfonate (EMS), or physical mutagens, such as UV light. Additionally, modern molecular biological techniques allow skilled persons to target specifically a gene by mutations. Using these techniques skilled persons are able to knock-out a specific gene or to introduce a new gene to generate a gain-of-function mutant.

On the transcriptional level, the synthesis of mRNA encoding a specific protein is controlled. A defect or change in gene transcription may switch-off or switch-on the mRNA synthesis of a specific enzyme. For example, methylation of DNA encoding an enzyme involved in sialic acid biosynthesis or modification, e.g. acetylation, of DNA-binding proteins, e.g. histones, transcription factors or proteins of the transcriptional machinery, could prevent transcription or could switch-on transcription of a specific gene. The induction of mutations by genetic and molecular biological methods described above and known to skilled persons are an option to affect transcription efficiency of any gene. The lack of UDP-GlcNAc-2-epimerase mRNA in NM-F9 cells, of which defect was generated by treatment of the wild type cells with the EMS mutagen, is one example for the impact of transcription to generate loss-of-function defects.

On the translation level, the synthesized mRNA of a specific enzyme is targeted, preferably to prevent or reduce ribosomal protein biosynthesis. Examples are the blocking of translation and/or degradation of a specific mRNA by RNAses using antisense molecules or small interfering RNA molecules that both target specific mRNA molecules. Both techniques are known to skilled persons.

On the protein level, a lack of enzyme activity could be caused by gene mutation. Possible mutations include the substitution, deletion and/or modification of at least one amino acid. The mutation may concern the catalytic properties of the enzyme either by structural re-folding of the protein, whereby the new and non-native structure does not allow binding of the substrate and/or converting same, or by changing residues within the active center which are responsible for interacting with the substrate. The techniques to generate such mutations are described above.

The CMP-sialic acid biosynthesis or transportation may also be affected by specific inhibitors. These inhibitors may be sialic acid analogues that block the activity of an enzyme or protein involved in the CMP-sialic acid biosynthesis or any transporter necessary for the transfer of a CMP-sialic acid. These inhibitors may bind to the regulatory and/or the catalytic center of the enzyme or protein, thereby preventing binding of the substrate and/or converting or transporting same. Inhibitors are molecules harboring a high binding affinity which are selected from the group comprising sialic acid analogues, small organic molecules, peptide ligands, antibodies and fragments thereof, DNA aptamers, RNA aptamers, Spiegelmers etc.

NM-F9 and/or NM-D4 cells that are deposited under DSM ACC2606 (NM-F9) and under DSM ACC2605 (NM-D4) at the "DSMZ-Deutsche Sammlung von Mikroorganismen and Zellkulturen GmbH" in Braunschweig (Germany), by Nemod Biotherapeutics GmbH & Co. KG, Robert-Rössle-Str. 10, 13125 Berlin (Germany) at the Aug. 14, 2003, are glycoengineered cells that turned out to be ideally suited expression cell lines for expression of highly active glycoproteins according to the invention and for use in the below described processes of the invention because NM-F9 and NM-D4 cells lost the ability to sialylate in a way that can be reconstituted by metabolic complementation. Therefore, in the present invention NM-F9 and/or NM-D4 cells are the most preferred cell lines with a defect in the defect in the sugar nucleotide biosynthetic pathway of sialic acids for the highly active glycoproteins and the below described processes of the invention.

Cellular defect in sialylation in NM-F9 and NM-D4 cells is caused by a lack of the UDP-GlcNAc-2-epimerase activity, whereby the sialylation can be restored by medium supplementation (also referred as metabolic complementation) with cellular products of the sialic acid biosynthesis upstream of the enzymatic reaction catalyzed by the epimerase, such sialic acid intermediates may be ManNAc, ManNAc-6-P, NeuAc-9-P, Neu5Ac and CMP-Neu5Ac. ManNAc is preferred. Surprisingly, the degree of the cellular sialylation could be controlled by the amount of ManNAc added to the cell culture medium, and not only the degree of cellular sialylation but even more surprisingly also of glycoproteins which are secreted or released from the cell can be regulated in that way. Surprisingly, the presence of sialylated serum proteins within the cell culture medium, mostly provided by addition of fetal calf serum (FCS) to the medium, influence the degree of sialylation of the cell or a secreted glycoprotein. This seems to be the case because the cell can, to some extent, apparently use sialic acids from up-taken glycoproteins for de novo glycosylation without requiring its own biosynthesis pathway to produce CMP-sialic acids or introduces by a catabolic way sialic acid into the known or an unknown precursor biosynthesis pathway of sialic acid. Therefore, a very low degree of sialylation is obtained when the cells are cultivated in FCS-free medium or even in a medium free of sialylated proteins. In presence of FCS the degree of sialylation is always higher than under the same cell culture conditions without FCS. Therefore, to achieve the highest sialylation degree in a given cellular system FCS or more preferably a sialylated glycoprotein, or most preferably the sialylated glycoprotein fetuin is added to the culture medium. In this way, the degree of sialylation on the NM-F9 cells or on a secreted glycoprotein could be controlled between below 20% sialylation, preferably below 10%, most preferably almost no sialylation compared to the original NM-wt cell sialylation, to complete sialylation (100%) compared to the original NM-wt cell sialylation without the epimerase defect.

In between this range the degree of sialylation can be differentially controlled by supplementing the medium with defined sugar intermediates, such as ManNAc in a concentration range from 0 to 200 mM, preferably 0 to 140 mM and more preferably 0 to 90 mM. To achieve very high degrees of sialylation sialoglycoproteins may be added to the medium. Each glycoprotein with a distinct degree of sialylation can be isolated and analyzed separately from the same glycoprotein but with a different degree of sialylation. Thereby a certain sialylation degree corresponds to a sialylation form which can comprise a single glycoform or a composition of glycoforms as described elsewhere in the present invention.

Therefore, the present invention provides a method or process for differential sialylation of glycoproteins, as described further below.

As described above, by analyzing the activity of each glycoprotein with a distinct degree of sialylation the optimized concentration of sialic acid precursor additive can be determined. The activity to be analyzed depends on the glycoprotein of interest. For example, in case said glycoprotein is a cytokine one would analyze the potential of the glycoprotein to stimulate immune cells preferably cells that are known to be stimulated by that cytokine, and more preferably cells that are used in a standard assay to determine the activity of said cytokine. When in another example said glycoprotein is a growth factor one would analyze the potential of the glycoprotein to induce cell proliferation, preferably of cells that are known to be stimulated by that growth factor, and more preferably of cells that are used in a standard assay to determine the proliferative activity of said growth factor. In a third example the serum half-life is of interest since it affects greatly the bioactivity of a therapeutically applied glycoprotein. The present invention allows the expression and isolation of various forms of one glycoprotein characterized by a distinct degree of sialylation, and by applying any assay to analyze any activity of said glycoprotein the optimal sialylation degree for the activity of said glycoprotein can be determined.

In the following glycoproteins and highly active glycoproteins are further described:

Examples of glycoproteins are mentioned above. Many of the aforementioned glycoproteins belong to the "cytokines" herein referring to the general class of hormones occurring in cells of the immune system, both lymphokines and monokines, and others. The definition is meant to include, but is not limited to, those hormones that act locally and do not circulate in the blood, and which, when used in accord with the present invention, will result in an alteration of an individual's immune response. Examples of further suitable immunomodulatory cytokines include, but is not limited to, interferons (e.g. IFN-alpha, IFN-beta and IFN-gamma), interleukins (e.g. IL-1, IL-2, IL-3, IL-4, IL-5, IL-6, IL-7, IL-8, IL-9, IL-10 and IL-12), tumor necrosis factors (e.g. TNF-alpha and TNF-beta), erythropoietin (EPO), FLT-3 ligand, macrophage colony stimulating factor (M-CSF), granulocyte colony stimulating factor (G-CSF), granulocyte-macrophage colony stimulating factor (GM-CSF), CD2 and ICAM. Taking erythropoietin, the molecule is believed to cause progenitor cells to mature into erythrocytes whereas thrombopoietin is thought to drive progenitor cells along the thrombocytic pathway. CSF refers to a family of lymphoicines which induce progenitor cells found in the bone marrow to differentiate into specific types of mature blood cells. The particular type of mature blood cell that results from a progenitor cell depends upon the type of CSF present. Similarly, granulocyte-macrophage colony formation is dependent on the presence of GM-CSF. Additionally, cytokines of other mammals with substantial homology to the human forms of IL-2, GM-CSF, TNF-alpha and others, will be useful in the invention when demonstrated to exhibit similar activity on the immune system. Similarly, proteins that are substantially analogous to any particular cytokine, but have relatively minor changes of protein sequence, will also find use in the present invention. It is well known that some small alterations in protein sequence may be possible without disturbing the functional abilities of the protein molecule, and thus proteins can be made that function as cytokines in the present invention but differ slightly from current known sequences. Finally, the use of either the singular or plural form of the word "cytokine" in this application is not determinative and should not limit interpretation of the present invention and claims. Adhesion or accessory molecules or combinations thereof may be employed alone or in combination with the cytokines.

Preferred glycoproteins are selected from the group comprising Glycophorin A, EPO, G-CSF, GM-CSF, FSH, hCG, LH, interferons, interleukins, antibodies and/or fragments thereof.

In the present invention the highly active glycoprotein may be an endogenous protein or preferably a protein which is produced recombinantly in the expression cell line. Therefore, the cDNA or gene encoding the glycoprotein of interest is cloned into an expression vector by molecular biological methods and expressed in the expression cell line. This expression is preferably a stable expression. All that techniques are known to skilled persons. There are many expression vectors available and suitable for expression in mammalian cells that are known to skilled persons. In an preferred embodiment the glycoprotein is secreted by the cell. Therefore the expression vector is constructed in a way which facilitates the secretion of the glycoprotein. Secreted glycoprotein can be a soluble glycoprotein or a membrane protein where the transmembrane domain is deleted. In a preferred embodiment nucleic acids encoding secretory signal peptides are comprised in the nucleic acid encoding the glycoprotein which enable, facilitate and/or increase the secretion of the proteins. Those signal peptides and their encoding nucleic acid is known to those skilled in the art. In an preferred embodiment of the invention the nucleic acid of the signal peptide has the sequence of SEQ ID NO: 1 or mutations, deletions, insertions and elongations of said sequence and fusion proteins containing said sequence.

In the present invention the recombinant expression of two highly active glycoproteins, granulocyte macrophage colony stimulating factor (GM-CSF) as a soluble protein and glycophorin A (GPA) as a membrane protein, in NM-F9 cells are given as examples.

GM-CSF is a potent species-specific growth factor of bone marrow cells playing an important role in the activation of innate and adaptive immune system. The factor stimulates the proliferation, development, differentiation and activation of granulocytes, macrophages, eosinophils and their progenitor cells. Furthermore, GM-CSF is crucial for the differentiation and maturation of dendritic precursor cells which are central to humoral and cellular immune responses. Synergistic actions are observed with erythropoietin (EPO) in proliferation of erythroid and megakaryotic progenitor cells, and with various other cytokines (e.g. IL-1, IL-3, IL-4, G-CSF). GM-CSF enhances microbicidal activity, oxidative metabolism, phagocytotic activity and cytotoxicity of neutrophils, eosinophils and macrophages, and induces the release of histamines and leukotriene C4 from basophils. There are several clinical indications for human GM-CSF which is applied as standard therapy while treating patients which undergo bone marrow transplantation, neutropenia, especially after chemo- and/or radiotherapy and cytopenia with regard to infections and hemorrhages after chemotherapy. Furthermore, it expanses the peripheral pool of stem cells for collection and induces susceptibility of leukemia cells causing acute myeloid leukemia and myelodysplastic syndromes to cell-cycle specific drugs during chemotherapy. Recombinant human GM-CSF supports the reconstitution of the hematopoietic system in the context of various diseases. In addition, there are several experimental therapies running, such as the combined GM-CSF/radiotherapy in cancer treatment which abolishes lethal effects of irradiation and restores hematopoiesis, and the combined GM-CSF/chemotherapy enhancing the tolerance to cytotoxic drugs (e.g. cancer chemotherapy, HIV) and enabling higher dosages and significant reduction of morbidity. rhGM-CSF is a promising adjuvant for cancer vaccines and cellular vaccines against cancer and infectious diseases, and a key component of dendritic cell based vaccines against tumors and infectious diseases. It is involved in adoptive T cell transfer as well. Generally, rhGM-CSF will enhance and stimulate the innate immune system.

Human GM-CSF of the present invention are more advantageous compared to GM-CSF produced by prior art due to their higher specific activities. This enhanced activity allows the use of less material per patient per dose and/or less administrations and/or reduced or lack of undesirable adverse effects, such as the capillary leak syndrome which has been observed during therapeutic use of recombinant GM-CSF, and/or lower costs for production.

In the present invention, rhGM-CSF is expressed recombinantly in UDP-GlcNAc-2-epimerase-deficient cells, such as NM-F9, and various forms of rhGM-CSF with a distinct sialylation degree between almost no sialylation and maximal sialylation were produced by metabolic complementation with increasing amounts of a sialic acid metabolites, preferably ManNAc, for example with 0-90 mM ManNAc in addition to the 90 mM ManNAc with 1 and 3 mg/ml of the sialoglycoprotein fetuin. To analyze the activity of the various sialo-forms of the rhGM-CSF a standard assay was chosen which determines the ability to stimulate cell proliferation, preferably of TF-1 cells and the human monocytic, dendritic cell line NemodDC (www.nemod.com). Surprisingly, the cell proliferation-stimulating activity of rhGM-CSF is strongly dependent on the degree of sialylation of rhGM-CSF with one sialo-form of rhGM-CSF showing highest activity that is highly but not maximally sialylated. The cell proliferation activity of commercially available rhGM-CSF, preferably Leukomax® and Leukine® expressed in bacteria and yeast, was tested in the same assay and found to be lower than the most active sialo-form expressed in NM-F9 cells. To achieve the maximal activity of Leukomax® or Leukine® up to 500 fold less of the optimal sialo-form from NM-F9 cells may be necessary in the according in vitro tests. When the activity was analyzed at the same concentrations of Leukine®, Leukomax® or the optimal sialo-form of rhGM-CSF the increase of activity was up to 1.5-fold, preferably two-fold, more preferably three-fold, most preferably four-fold, and highly preferably five-fold. These findings are especially surprising the prior art did not prove that the activity of rhGM-CSF is dependent of its glycosylation.

Additionally to the higher activity found for the optimal sialo-form of rhGM-CSF the relatively high sialylation degree of that sialo-form guarantees a longer serum half-life when applied therapeutically. Advantageously, lower doses within longer time intervals are administered, accompanied by the reduction or the complete abolition of immunogenicity and adverse effects. The latter two are additionally affected in a positive manner by the human-related glycosylation pattern. The high degree of sialylation of the highly active rhGM-CSF largely improves pharmacokinetic properties.

The present invention provides the highly active glycoprotein secretory rhGM-CSF which can be used advantageously as above described in the various clinical applications but also in in vitro applications, for example for generation of differentiated dendritic cells and activated T cells.

The new technology of the present invention is also of great benefit for the improvement of other growth factors and hormones, such as EPO, FSH and hCG, and for the improvement of various other glycoproteins, such as cytokines and antibodies as outlined above, and others as described elsewhere in the present invention.

As another example, Asialoglycophorin A (AGPA) was recombinantly expressed in NM-F9 cells. Based on Glycophorin A (GPA) which was isolated from blood samples and thereafter enzymatically desialylated resulting in exposure of the Thomsen-Friedenreich (TF, core-1) antigen a successful vaccine was developed for treatment of TF-positive tumors.

GPA and AGPA are integral membrane proteins. For establishment of a production process it would be highly advantageous to express a recombinant fragment of GPA which could be secreted into the cell culture medium by any cell line, preferably by NM-F9 and NM-D4 cells. Therefore, the expression vector secGPA was constructed encoding a GPA-fragment containing the extracellular glycosylated domain of GPA and lacking the transmembrane domain and the intracellular domain of GPA. First experiments revealed that only small amounts of secretory AGPA were detectable in the medium of stably transfected NM-F9 cells (see examples). To increase the secretion rate several heterologous signal peptides have been fused to the GPA fragment, whereby the endogenous signal peptide has been eliminated. Surprisingly, the signal peptide derived from GM-CSF comprising the amino acid sequence characterized by SEQ ID NO: 1 was the most effective signal peptide compared with the endogenous signal peptide of GPA and the other heterologous signal peptides derived from a T-cell receptor and the antibody kappa light chain. Only the latter two signal peptides are available to and known by skilled persons for use in recombinant expression of secretory proteins.

The present invention provides the highly active glycoprotein secretory Asialoglycophorin A expressed or produced by any cell or cell line that is defective in sialylation, preferably said cells are human cells, more preferably said cells are NM-F9 or NM-D4 cells, carries the TF-antigen in preferable densities without masking by sialylation. When used as an anti-tumor vaccine in murine models it elucidates a strong anti-TF and anti-tumor response and it also shows the potent TF-specific anti-tumor response in human in vitro studies which is not achieved by the sialylated or other glycosylation forms of the GPA showing that this is a highly active glycoprotein form in the sense of the invention. Its potent anti-tumor response shows that it can be used effectively as a potent anti-tumor vaccine component against TF-specific tumors in a curative or prophylactic setting.

The TF carbohydrate is a well-known tumor antigen present on many tumor tissues but not on normal cells of healthy human beings. Glycophorin A (GPA) is a carrier of the TF antigen masked by sialylation. Based on GPA which was isolated from blood samples and thereafter enzymatically desialylated resulting in exposure of the TF antigen a successful vaccine was developed for treatment of TF-positive tumor patients. In the present invention only the extracellular domain which is also the only glycosylated part of GPA is produced recombinantly in human cells that are defective in sialylation, preferably in NM-F9 and NM-D4 cells in a secretory form (secGPA, see above). The advantage of using sialylation defective cells, such as NM-F9 or NM-D4 cells, is that the TF antigen present on GPA expressed in any form in that cells is free of sialic acids and therefore, can be used as a defined, standardizable vaccine without enzymatic pretreatment.

The invention also provides a nucleic acid comprising the nucleic acid sequence encoding the glycoprotein and the nucleic acid sequence of SEQ ID NO: 1 or mutations, deletions, insertions and elongations of said sequence and fusion proteins containing said sequence. The signal peptide derived from GM-CSF characterized by SEQ ID NO: 1 or mutations, deletions, insertions and elongations of said sequence and fusion proteins containing said sequence can be used to drive the secretory expression of any mammalian gene product, such as GPA, in mammalian cells, preferably in human cells, more preferably in subclones of NM-wt cells, and most preferably in NM-F9 and NM-D4 cells. Said signal peptide is integrated into the protein of interest by techniques that are known to skilled persons, e.g. by molecular cloning of nucleotide sequences encoding the signal peptide into the cDNA encoding the protein of interest in frame of the coding region. Thereby the endogenous signal peptide is completely or in part eliminated. When this construct is subcloned into any expression vector known to skilled persons and introduced into cells by any method known to skilled persons, such as by chemical transfection, lipofection, electroporation or infection, a fusion protein is synthesized by the cell comprising said signal peptide and the protein of interest. During processing of this fusion protein in the cell the signal peptide is completely or in part removed.

According to the present invention the term "glycoprotein" is also defined as a virus, a virus particle, or a viral protein. Viruses, virus particles or viral proteins that can be produced according to the invention include such from enterovirus, e.g. rhinovirus, poliomyelitisvirus, or aphtovirus; herpesvirus, e.g. herpes simplex virus, pseudorabies virus, or bovine herpes virus; orthomyxovirus, e.g. influenza virus; pestivirus; rhabdovirus; paramyxovirus, e.g. newcastle disease virus, respiratory syncitio virus, mumps virus, or a measles virus; retrovirus, e.g. human immune deficiency virus, a parvovirus or papovavirus; rotavirus; coronavirus; flavivirus, e.g. yellow fever virus or tick-borne encephalitis virus; hepatitis causing virus, e.g. hepatitis A or hepatitis B virus.

A highly active virus, a virus particle, or a viral protein in sense of the invention has advantages which can be determined by a suitable bioassay, such as the measurement of infectivity of particular expressed sialylation forms of the virus, a virus particle, or a viral protein, the potency of particular expressed sialylation forms of the virus, a virus particle, or a viral protein as a vaccine or vaccine component, the productivity of particular expressed sialylation forms of the virus, a virus particle, or a viral protein or other beneficial medical more biological features known to those skilled in the art. The according bioassay can be selected, adopted or build up by those skilled in the art by using the present invention. Preferably the infectivity of a produced virus is optimized by differential sialylation resulting in an improved vaccine. This allow the optimization of the sialylation degree of said virus, virus particle, or viral protein.

Preferably the human cell line NM-F9 or NM-D4 is used producing a highly active human virus, a virus particle, or a viral protein for use in vaccines. The human cell lines are capable of normal post- and peri-translational modifications and assembly such glycosylation and allows the optimization of the sialylation and sialylation degree as described elsewhere in the invention.

It is known that the sialylation of viruses often play an important role in the infectivity of the virus. By optimizing the sialylation degree safer and/or more potent viral vaccines can be produced. In addition, this and/or a higher production can lead to improved and hence cheaper product processes.

The present invention also provides a process for the production of a highly active glycoprotein comprising expression of said highly active glycoprotein in an expression cell line, harboring at least one defect in the sugar nucleotide biosynthetic pathway of sialic acids and which is transfected with nucleic acid encoding the glycoprotein, in a medium supplemented with a concentration of at least one sialic acid precursor additive, the concentration being determined by a process comprising:

(i) expression of a plurality of different sialylation forms of said glycoprotein by differential sialylation using different concentrations of at least one sialic acid precursor; and (ii) determination of the activity of the different sialylation forms in comparison with a reference glycoprotein in (a) suitable bioassay(s); and (iii) selection of the sialylation form with the higher/highest activity and determination of the concentration of the sialic acid precursor additive(s) which is correlated with the higher/highest activity level of said glycoprotein.

The above described process allows the production of the optimal sialylation form of a glycoprotein which was determined as the highly active glycoprotein. For those skilled in the art by using the processes of the invention it is possible and relatively easy to transfer the conditions determined at an analytical or pilot scale grade to the production scale and to adjust and improve growth and media conditions. An additional advantage of the present process over other process is that during the up-scaling procedure which can be connected with an improved productivity the desired sialylation degree of the highly active protein can be stabilized by adapting the concentrations and composition of sialic acid precursor additives in addition to optimization of other media components.

All definitions and descriptions described above for highly active glycoproteins in sense of the invention are also valid for the above and below described processes.

Furthermore, the invention provides a process for the identification/determination of a highly active glycoprotein comprising:

i) transfection of expression cell line harboring at least one defect in the sugar nucleotide biosynthetic pathway of sialic acids with nucleic acid encoding the glycoprotein; and ii) expression of a plurality of different sialylation forms of said glycoprotein by differential sialylation using medium with different concentrations of at least one sialic acid precursor additive; and iii) determination of the activity of the different sialylation forms in comparison with a reference glycoprotein in (a) suitable bioassay(s); and iv) selection of the sialylation form with the higher/highest activity.

In principle said process can be used as analytical tool (i) to analyze whether there is any correlation between the activity of a given glycoprotein and its degree of sialylation, (ii) to determine what might be the optimal sialylation form of a given glycoprotein with respect its activity and (iii) to determine the conditions to produce the optimal sialylation form.

Furthermore, the invention is useful for investigating the role of human glycosylations, preferably sialylations, in the bioactivity.

Additionally provided is a process for differential sialylation of a glycoprotein, characterized in that, an expression cell line harboring at least one defect in the sugar nucleotide biosynthesis pathway of sialic acid is transformed with a nucleic acid encoding the glycoprotein, whereby the cells are cultured in a media supplemented with a plurality of different concentrations of at least one sialic acid precursor additive, and a plurality of different sialylation forms of the glycoprotein is obtained.

The invention also provides processes for the identification/determination of highly active virus, virus particle, or viral protein, its production and its differential sialylation as well as the highly active virus, virus particle, or viral protein resulting from a process provided by this invention.

All definitions and descriptions described above for highly active glycoproteins in sense of the invention are also valid for the above and below described processes.

The present invention is preferably embedded in a technology platform based on GlycoProfiling, GlycoEngineering, GlycoAnalytics, and GlycoExpress, where GlycoProfiling is understood as a range of techniques to analyze the cellular glycosylation machinery and carbohydrates produced by the glycosylation machinery, preferentially present on the cell surface, with the aim to choose an appropriate cell for GlycoEngineering.

GlycoEngineering is understood as a range of techniques to modify the glycosylation machinery of a cell resulting in a cell with a modified GlycoProfile.

GlycoAnalytics is understood as a range of techniques to analyze the glycosylation of proteins on the molecular level.

GlycoExpress comprises the below described technologies and processes of the invention including differential sialylation, identification and determination of highly active proteins and the production of highly active glycoproteins.

The advantage of combining the here mentioned technologies comprising the glycoproteins and processes of the invention allows higher improved highly active proteins, better expression cell line systems in the sense of the invention, their analysis and production. Other advantages are speed, costs, stability and effectivity of the processes and products.

All definitions and descriptions described above are also valid for the above and below described glycoproteins and processes.

Another advantage of the present invention is the combination of its processes which resembles an integrated system in order to generate highly active glycoproteins with optimized sialylation in respect to the use and function of the glycoprotein. Such a combination is described in a preferred example in the following but is not restricted to this.

In a first step the nucleic acid encoding the glycoprotein, preferably a secreted form, preferably comprising a sequence according to SEQ ID NO: 1, and even more preferred human GM-CSF or GPA, is transfected into an expression cell line with defect in the sugar nucleotide biosynthetic pathway of sialic acids, preferably using NM-F9 or NM-D4, preferably by electroporation, and stable expressing clones are selected, preferably by single cell cloning, and preferably those which grow in serum-free and even more in protein-free medium.

In a second step, different sialylation forms of said glycoprotein are generated by differential sialylation, preferably a series of at least 2, more preferred more than 2, more preferred more than 3, even more preferred more than 4 different sialylation forms, by using different concentrations of at least one sialic acid precursor. The higher active glycoforms are determined by at least one bioassay, such as a cellular proliferation in vitro assay as for human GM-CSF or an immunization in vivo test using mice or humans for showing the higher specific immunogenicity against certain tumor cells as for GPA. In a preferred form a combination of bioassays is used for determining the highly active glycoprotein with the highest activity which depends on the use of the glycoprotein. As described elsewhere in this invention, the selected highly active glycoprotein does not have to be better in all bioassays and the higher activity or improved feature in one bioassay can be sufficient, however, preferably the selected highly active glycoprotein is better in at least two bioassays for example in one in vitro model, such as proliferation assay, and/or a higher activity in at least one in vivo model and/or a higher stability and/or a longer serum half-life and/or a longer bioavailability and/or an improved immunogenicity and/or an improved antigenicity. Most preferred are such which have a higher bioactivity in vivo in humans which can be due to a combination of different features such as a higher activity in the receptor mediated function as well as an improved bioavailability by expressing a longer serum half-life. For example the rhGM-CSF sialylation form generated by using NM-F9 and 90 mM ManNAc as a sialic acid precursor additive in medium under the described conditions, showed the highest activity and hence is a preferred highly active glycoprotein.

It can be advantageous in respect to speed and resource to select a smaller group of sialylation forms of a glycoprotein from a larger set by one bioassay for further test in another bioassay. In the case of GPA it is sufficient to generate only one sialylation form namely such with the lowest sialylation and hence without sialic acid precursor additive in a serum-free medium (see also above and below). In this, the resulting highly active GPA can be compared with sialylated GPA from human sources which shows a much higher activity which is here a higher immunogenicity resulting in a strong anti-TF immune response in animal models and in humans. However, preferably also at least another sialylation form is generated by the process of the invention and compared in the bioassay.

The integrated system allows after the above described determination of the highly active glycoprotein to use the same expression cell line with the transfected nucleic acid encoding the glycoprotein and by using the corresponding concentration of sialic acid precursor additive for producing the said highly active glycoprotein. For the production of the highly active glycoprotein often an up-scaling is wanted. For this optimal conditions of the sialic acid precursor additive may be sufficient, however, by optimizing for example other media components and using different reaction vessels it might be advantageous or even necessary to adjust said sialic acid precursor additive in concentration and composition in order to stabilize the wanted sialylation degree of the highly active glycoprotein. This can be achieved by a person skilled in the art by using the present invention. The ability to stabilize the sialic acid degree by adjusting the sialic acid precursor additive is a large advantage of the process which is not achieved by conventional expression systems of the prior art.

The integrated system allowing to use virtually the same or similar processes for identification and production of the highly active glycoproteins, has beside others the obvious advantage of higher speed and lower costs.

The integrated system is particularly advantageous and powerful when combined with other processes, technologies and methods as described elsewhere in the invention for example under GlycoProfiling, GlycoEngineering and GlycoAnalytics.

To generate an expression cell line with a defect in the sugar nucleotide biosynthetic pathway of sialic acids whereby the defect is reconstituable is very difficult, because (i) many enzymes are involved in sialylation, meaning that elimination of a single enzyme activity will not necessarily affect the capacity of a cell to sialylate, (ii) many of the enzymes are redundant, meaning the loss of one enzyme activity is often compensated by an other enzyme, (iii) the reconstitution of the defect is often not possible, and (iv) the metabolic complementation of the defect is often not possible. The invention provides a novel process for the generation of an expression cell line with a defect in the sugar nucleotide biosynthetic pathway of sialic acids comprising the selection of an expression cell line from primary cells or cell lines with a recognition molecule that binds, preferably, to desialylated structures which can be sialylated by at least two enzymes.

In an preferred embodiment the cells from primary cells or cell lines are mutagenized before selection. The mutagenesis can be performed by random mutagenesis by chemical or physical means or directed mutagenesis as described elsewhere in the invention or known to those skilled in the art.

In contrast to the process of the invention, with current processes known to those skilled in the art it is very difficult, time consuming and often not possible to generate cells with a genetic defect in the sialic acid precursor pathway, especially when the target gene is not known.

The selection is performed by enrichment and/or isolation of the cell or cells by using at least one of the described recognition molecules with technologies known to those skilled in the art for example via affinity chromatography, using for example the magnetic cell sorting technology (MACS technology) or immunoprecipitation or chromatography, and/or by cell sorting by flow cytometry and/or by identification of the cells with the property of binding to at least one recognition molecule, for example by flow cytometry or immunocytochemistry or by biochemical analysis of secreted proteins.

The selected cells can be used as an expression cell line or are preferably further cloned by known technologies in order to generate a pure clone, for example by single cell cloning.

Surprisingly the usage of recognition molecules which target desialylated structures which can be sialylated by at least two enzymes enables and/or strongly bias the selection towards those cells which have defects in those enzyme activities which can be reconstituted by metabolic substances, a prerequisite for metabolic control of the sialylation degree in a expression cell line.

The process of the invention enables a generation of such cell lines at all or greatly facilitates their generation in sense of speed, reduced amount of work and/or probability of success. This is particularly but not only the case for human cell lines.

The process of the invention is especially suitable when the target gene for mutagenesis is not known and the selection is based on the phenotypic effect of down-regulation of sialylation. But it is also advantageous when a directed mutagenesis is used, for example a knock-out of the GlcNAc-epimerase activity by site-directed recombination, by greatly facilitating the selection of stably mutagenised clones via the phenotypic down-regulation of sialylation.

These generated cell lines can be made for the purpose of the differential sialylation or the as expression cell lines in sense of the invention, however, they can also be used for other purposes where they are beneficial or usable.

To generate cell lines that are defective in the ability to sialylate with the option to reconstitute that defect, in principle every mammalian cell line is applicable. For a production process biotechnologically suitable cell lines are preferred, such as Per.C6, HEK293, K562, CV1, COS-7, Hybridoma cells, Namalwa, BHK and CHO. The method of choice to generate new cell lines with said defect is the above described process which belongs to our GlycoEngineering technologies.

Before starting with the described process to generate a cell line with said defect it is very useful to characterize at least partially the glycosylation machinery of candidate cell lines (GlycoProfiling). For this at least one of the following technologies but preferably a combination of such technologies are preferred to be used which can analyze (i) the mRNA expression of relevant genes of glycosylation machinery, such as sialyltransferases, transferases of enzymes important for carbohydrate structures which are substrates for sialyltransferases, transporters, epimerases, sialidases and others described elsewhere in the description of the invention mentioned earlier, (ii) the enzymatic activity of relevant enzymes, preferably sialyltransferases, (iii) the determination of carbohydrate determinants which can be sialylated or which are sialylated by appropriate recognition molecules. GlycoProfiling helps to understand the glycosylation machinery of a candidate cell line which allows to decide about a strategy for modification of the glycosylation machinery (GlycoEngineering). For example, the mRNA expression profiles of enzymes and proteins involved in glycosylation, such as glycosyltransferases, enzymes of the monosaccharides biosynthesis and transporters, of candidate human cell lines, such as ZR75-1, HEK293, NM-wt (K562), KG1, LS174T, MCF-7, SW480 and T47D, were analyzed by RT-PCR. Bioassays were used to analyze the enzyme activities, preferably sialylatransferase activities, of candidate cell lines. Bioassays are also used to analyze carbohydrate determinants, preferably those which are or can be sialylated by at least two enzymes, by appropriate methods, such as flow cytometry and/or immunofluorescence-microscopy, using specific antibodies and lectins preferably in combination with sialidases or other methods removing or destroying the sialic acids, such as mild periodate oxidation. Suitable bioassays are known or can be adjusted or developed to those skilled in the art.

According to the present invention the term "primary cells or cell lines" comprises all cells, including for example those from biological specimen like, for example blood cells, cells from tissues or other sources, as well as existing cell lines. Cells and cell lines can consist of a defined clone origination from a single cell or a mixture of cells as sometimes seen with declared cell lines. The cells can be already immortalized or can be immortalized as an extend part of the process of the invention. The immortalization can be spontaneous, for example for cells gained from a tumor source, or can be immortalized by technologies known by those skilled in the art, for example viral transformation, whereby those skilled in the art are able to determine the best time point of immortalization which can depend on the particular cell. The cells can also be or become modified by or in other genes.

According to the present invention the term "defect in the sugar nucleotide biosynthetic pathway of sialic acids" means the same defects as described elsewhere in the description of the invention.

According to the present invention the term "recognition molecules" means molecules that bind preferably and/or specifically to molecules which are partially or preferably completely desialylated and which can be sialylated by at least two enzymes. Preferred molecules are lectins and even more preferred are antibodies recognizing according carbohydrate structures. Even more preferred are antibodies which bind TF (Thomsen-Friedenreich, core-1) such as Nemod-TF1, Nemod-TF2, A78-G/A7, or that recognize terminal galactose residues, or lectins such as RCA, ECL, PNA, Jacalin, ACA, BPL or Amaranthin or those which bind sialic acids such as SNA and MAA or by PankoMab.

In a more preferred embodiment the desialylated structures to which the recognition molecules bind can be sialylated by alpha2-3 and alpha2-6 bound sialic acids.

In an even more preferred embodiment the structures to which the recognition molecules bind are O-Glycans.

In an even more preferred embodiment the structure to which the recognition molecules is the core-1 structure (GalNAc alpha 1-3Gal) also called Thomsen-Friedenreich (TF) structure.

In an even more preferred embodiment the process for the generation of an expression cell line with a defect in the sugar nucleotide biosynthetic pathway of sialic acids comprises the selection of an expression cell line from primary cells or cell lines with an antibody recognizing the Core-1 structure.

In an even more preferred embodiment the primary cells or cell lines are mutagenised before selection.

As an example, an expression cell line harboring a defect in the sugar nucleotide biosynthetic pathway of sialic acids according to the present invention was generated by engineering NM-wt cells. Based on the glycosylation profile of a number of candidate cell lines revealed by GlycoProfiling (see above) a cell line is selected for GlycoEngineering to generate TF-positive cells. Preferably the chosen cell line is negative for C2GNT-L or -M, more preferably positive for cryptic TF, even more preferably able to sialylate at a very high degree with []-2,3 and []-2,6 linked sialic acids, and most preferably the cells are NM-wt cells. Briefly, the cells are analyzed for TF expression by any method available to skilled persons, preferably by flow cytometry or immunocytochemistry (described in the example). TF-positive cells are selected by using the monoclonal antibodies A78-G/A7 or PankoMab. In case, the number of TF-positive cells is to low, the TF-negative cell line is treated with a mutagen, preferably a chemical mutagen, preferably ethyl methanesulfonate (EMS). Thereafter, the TF-positive cells are selected as described above. The selection for TF-positive cells need to be repeated and thereafter TF-positive cells need to be cloned to receive cells that are stably TF-positive. In that way NM-F9 and NM-D4 cells were generated.

With a similar adapted approach it is possible to glycoengineer any cell line to receive a new cell line with a new GlycoProfile for use for instance in production of glycoproteins with a defined glycosylation profile. Such profiles could be an improved sialylation, a more human glycosylation, a glycosylation resembling the native glycoprotein or a less or more immunogenic glycosylation.

In the following pharmaceutical compositions or compositions of glycoproteins and highly active glycoproteins and their use are further described:

The present invention relates to a composition or a pharmaceutical composition of highly active glycoproteins of the present invention for in vivo or in vitro use, comprising a glycoprotein of the invention, and a diluent or carrier. Mammalian glycoproteins as described in the present invention and compositions thereof can be used in a wide range of applications that are defined by the nature of the glycoprotein. In all these applications the use of a highly active glycoprotein will be always of great benefit. For example, mammalian glycoproteins according to the invention can be used in in vitro assays, such as cellular and immunological assays of any kind, or analytical assays, such as ELISA or RIA. Having GM-CSF as an example of a glycoprotein preferred in the present invention, this growth factor can be used in vitro to induce the proliferation and/or differentiation of certain immune cells, such as dendritic cells or macrophages, which are then used in certain immunological assays, such as ELISPOT-, T-cell-, cytotox-, cell migration-, cell adhesion-, or phagocytosis-assays. GM-CSF according to the invention can be also used directly in cell proliferation assays.

The highly active mammalian glycoproteins described in the present invention and compositions thereof are also useful for diagnostic purposes. For example, the optimal sialylation form of a glycoprotein could be produced as standard for diagnostic purposes. Preferred is the in vivo application of highly active mammalian glycoproteins described in the present invention and compositions thereof. The wide range of in vivo applications, such as prophylactic and/or therapeutic treatment of infections of any kind, cancer, leukemia, diseases of the hematopoietic systems, neutropenia, cytopenia, myelodysplastic syndromes and autoimmune diseases, of highly active mammalian glycoproteins according to the present invention is defined by the nature of the specific glycoprotein and is known to people of the field of art. The origin of said glycoprotein decides in which mammalian species the glycoprotein is applied for in vivo use. For example, bovine GH is used for treatment of cows to increase the milk production. The application of highly active bovine GH according to the invention will improve that treatment, since the number of applications and undesired side effects are expected to decrease.

In human beings glycoproteins as described in this invention are used therapeutically. Using highly active glycoprotein will be always of great benefit, because the number of administrations and undesired side effects are expected to decrease. For administration to patients, the purified glycoproteins of the present invention are mixed with a pharmaceutically acceptable carrier or diluent in accordance with routine procedures. Therapeutic formulations will be administered by intravenous infusion or by subcutaneous injection, or by any other acceptable method known to the field of art. The formulations can also contain, if desired, other therapeutic agents. The amount, frequency and period of administration will vary and depend upon a variety of factors including the activity of the specific compound employed, the age, body weight, general health, sex, diet time of administration, route of administration, rate of excretion, drug combination and the severity of the disease-specific therapy. The amount of active ingredient that is combined with the carrier materials to produce a single dosage form varies depending upon the host treated and the particular mode of administration.

In a preferred embodiment of the present invention, said pharmaceutical composition is a vaccine or vaccine-adjuvant. In accordance with the present invention, the term vaccine composition relates to any composition which can be used as a vaccine in mammals and humans. A vaccine means a therapeutic or prophylactic use of the pharmaceutical composition which induces an immune response. The forms or methods for manufacturing vaccine compositions according to the present invention are not particularly limited, and a composition in a desired form can be prepared by applying a single method available in the field of the art or methods in an appropriate combination. Administration of any vaccine and/or vaccine-adjuvant can be subcutaneous, intradermal, intravenous, parenteral, intramuscular, or by any other acceptable method. The formulations and pharmaceutical compositions contemplated by the above dosage forms can be prepared with conventional pharmaceutically acceptable excipients and additives, using conventional techniques. Other adjuvants may be administered either with the vaccine or together with the glycoprotein.

An example for a human tumor vaccine represents Asialoglycophorin A (AGPA). Glycophorin A (GPA) is a sialylated glycoprotein located in the membrane of erythrocytes and also found in some cell lines. For vaccine production it is isolated from human blood preparations and treated enzymatically to eliminate all sialic acids bound to GPA. The resulting AGPA is carrier of the tumor-specific carbohydrate antigen Thomsen-Friedenreich (TF) and therefore applied as a vaccine to induce a sustained immune reaction against TF and thereby to eliminate or at least to reduce the TF-positive tumor load of a patient. The use of sialylation defective cells as described in the present invention allows now the recombinant production of AGPA without the necessity of an enzymatic treatment and without being restricted to use human blood preparations for production. AGPA is one example for the use of a glycoprotein and a pharmaceutical composition thereof as a vaccine for immunotherapy of tumor and cancer patients.

Additionally, the invention provides a highly active viral protein, virus particle, and/or virus resulting from a process provided by this invention for use in vaccines, especially when brought in a pharmaceutical composition including suitable excipient and/or adjuvants. Dosage and way of administration can be determined through preclinical and clinical development by those skilled in the art.

Vaccine-adjuvants are typically used to enhance the protection afforded by animal or human vaccines that are considered weak (i.e. by providing diminished protection in terms of level, extent, and/or duration). Examples for glycoproteins that are used as vaccine-adjuvant, are GM-CSF and certain cytokines, such as IL-2 and IL-7. The glycoprotein as vaccine-adjuvant can be administered separately from the vaccine or in combination with the vaccine as well. When a glycoprotein as vaccine-adjuvant is combined with the vaccine, the composition administered contains an immunogen that is effective in eliciting a specific response to a given pathogen or antigen, a pharmaceutically acceptable vaccine carrier and an immunopotentiating amount of glycoprotein. An example for that concept are whole cell vaccines known to the field of the art where the vaccine-adjuvant is recombinantly expressed by the cell that is the carrier of the antigen. Whole cells vaccines are typically applied as vivid cells that are committed to cell death. After vaccination these cells produce for certain time period certain amounts of glycoprotein, such as GM-CSF, IL-2 or IL-7, that act as vaccine-adjuvant. Whole cell vaccines may also be killed before vaccination having still the advantage of a whole cell vaccine however without the option that vaccine-adjuvants are additionally produced by the whole cell vaccine after vaccination. The present invention provides not only the vaccine-adjuvant, but also the cell line or cell lines used as whole cell vaccine can be generated by a procedure provided by the present invention. Characteristic for cells used for a whole cell vaccine is that such a cell line or a combination of cell lines express as many antigens as possible. As known to everybody of the field of art, these cells or combination of cell lines can be vaccinated directly or loaded onto antigen-presenting cells, such as dendritic cells, by methods known to the field of art. The antigen-loaded dendritic cells are then used for vaccination or are used to stimulate T-cells ex corpore for an adoptive T-cell therapy by methods known to everybody skilled in the art. In the present invention said vaccine can be a cell line or a combination of cell lines that were produced by a process described in the present invention and that expresses the glycoprotein of the present invention as vaccine-adjuvant.

Glycoproteins or a pharmaceutical composition thereof can be used as vaccine or vaccine-adjuvant for treatment of infectious diseases, such as AIDS, SARS or certain forms of hepatitis. The mammalian glycoprotein is part of attenuated live or killed virus products or recombinant antigenic viral products that are produced according to the present invention and that induce immune responses against infected cells for treatment of human infectious diseases, such as HIV, SARS, hepatitis B or influenza A and B, or infectious diseases of animals, such as bovine virus diarrhea, equine influenza, feline leukemia, feline respiratory disease.

The present invention relates to a kit comprising a glycoprotein of the invention, and/or a pharmaceutical composition thereof, and/or analogues, modifications and pharmacologically active fragments thereof and optionally, an information about how to use the kit. In a preferred embodiment of the present invention, the kit can be used for enhancing an immunogenic response of a mammal to antigens in a vaccine comprising a container of a pharmaceutical composition of highly/higher active glycoprotein, such as GM-CSF, EPO or FSH and a pharmaceutically acceptable carrier therefore, and a container of a pharmaceutical composition of a vaccine and a pharmaceutically acceptable carrier therefore.

Glycoproteins of the present invention can be used as vaccine or vaccine-adjuvant for treatment of infectious diseases. Additionally, the glycoproteins of the present invention can also be used for the manufacture of a vaccine or vaccine-adjuvant for treatment of infectious diseases.

Glycoproteins of the present invention can be used for prophylactic and/or therapeutic treatment of diseases, such as leukemia, neutropenia, cytopenia, cancer, bone marrow transplantation, diseases of hematopoietic systems, infertility and autoimmune diseases. The spectrum of therapeutic applications known to people of the field of art, of glycoproteins is very wide. For example, G-CSF is an important therapeutic to treat neutropenia, a life-threatening decrease in neutrophils as consequence of a chemotherapy of leukemic cancer patients. GM-CSF is specifically used for treatment of AML patients at relative high age after chemotherapy to achieve a fast recovery from neutropenia. GM-CSF is additionally approved as therapeutic for several applications in bone marrow transplantations and for mobilization of peripheral blood stem cells. In addition, there are several clinical applications of GM-CSF that are currently under investigation, such as for treatment of HIV and cancer. Certain diseases of the hematopoietic system are treated with EPO, and IFN-beta is currently an important therapeutic for treatment of multiple sclerosis, an autoimmune disease. An other example is FSH which is widely used for treatment of male and female infertility. hCG is also applied for the treatment of infertility, but focusing on the anovulation in women. hGH has clinically-proven benefits, such as bodyfat reduction and muscle tissue increase.

Glycoproteins of the present invention can also be used for the manufacture of a medicament for prophylactic and/or therapeutic treatments of diseases selected from the group comprising leukemia, neutropenia, cytopenia, cancer, bone marrow transplantation, diseases of hematopoietic systems, infertility and autoimmune diseases.

The glycoprotein of the present invention, the vaccine or the medicament can be used by any conventional administration route such as, for example, via parenteral, ocular, topical, inhalation, transdermal, vaginal, buccal, transmucosal, transurethral, rectal, nasal, oral, pulmonary or aural routes.

An other example for therapeutic glycoproteins according to the invention are antibodies. Antibodies act by binding specific targets with high affinity. When linked to a toxin or a radioactive isotope antibodies are a powerful therapeutic directed against tumor cells or infected. However, also "naked" antibodies are able to mediate the elimination of particular or cellular targets by directing specific immune cells (ADCC) or complement (CDC) with cytotoxic and/or phagocytotic activity to the target. Especially the ADCC and/or CDC activity of antibodies can be improved by an appropriate change in the glycosylation of a given antibody.

It is to be understood that this invention is not limited to the particular methods, compositions, and cell lines described herein, as such methods, compositions, and cell lines may, of course, vary. It is also to be understood that the terminology used herein is for the purpose of describing particular embodiments only, and is not intended to limit the scope of the present invention which is only defined by the appended claims.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" or "a process" includes reference to equivalent steps, methods, or processes known to a person of ordinary skill in the art, and so forth.

Unless otherwise defined, all technical and scientific terms used herein have the same meaning as commonly understood by a person of ordinary skill in the art to which this invention belongs. Although methods, processes and materials similar or equivalent to those described herein can be used in the practice or testing of the present invention, suitable methods and materials are described below.

The following tables 1 and 2, and figures illustrate the present invention for the production of highly active human proteins with an optimized sialylation.

Table 1: Expression profiles of glycosyltransferases in different human cell lines. Given values are in percentage and relative to that of ZR75-1. In each case, duplex RT-PCR was used for the determination of glycosyltransferase mRNA expression versus the housekeeping beta-actin control.

Table 2: Detection of carbohydrate determinants in different human cell lines by means of monoclonal antibodies and lectins. Given values are substractive means of antibody/lectin binding versus isotype or secondary reagent as negative control determined by flow cytometry analysis. For example, monoclonal antibody A78-G/A7, and lectins PNA (peanut agglutinin) and *Artocarpus integrifolia* Jacalin are TF-specific. Treatment of cells with neuraminidase (highlighted in white) caused TF exposure enabling affinity binding.

BRIEF DESCRIPTION OF THE DRAWINGS

The invention will now be described with greater detail with reference to the drawings, wherein:

FIGS. 3A-B: Determination of membrane glycoconjugate-bound sialic acid on NM-wt cells, and derivatives NM-F9 and NM-D4 (FIG. 1A) by flow cytometry using the lectins PNA, SNA, MAA and UEAI, or (FIG. 1B) by thiobarbituric acid method.

Figure 1A:
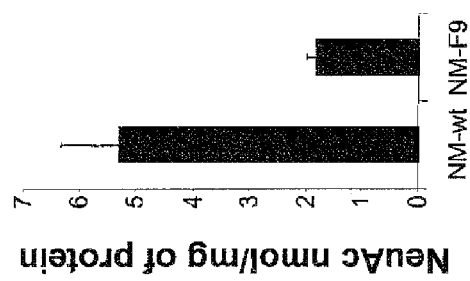
FIGS. 1A-C: GlycoEngineering of NM-wt cells and characterization of resulting NM-F9 cells. Random mutagenesis was performed by EMS treatment. Exposure of desialylated epitopes enabled affinity selection and subsequently cloning of EMS-treated NM-wt cells resulting in cell clones with high exposure of TF structures determined in immunocytochemistry using the TF-specific antibody A78-G/A7 (FIG. 1A, upper panel: EMS-treated NM-wt cells; lower panel: affinity selected and cloned NM-F9 cells). The sialylation degree was determined (FIG. 1B) by flow cytometry applying the TF-specific antibody A78-G/A7, the terminal []-Gal recognizing lectin PNA and the sialic acid specific lectin SNA, or (FIG. 1C) by the thiobarbituric acid method.

The following examples are provided by way of illustration and not by way of limitation. Within the examples, standard reagents and buffers that are free from contaminating activities are used. It is preferred to exercise care to avoid ribonucleases and PCR product contamination.

EXAMPLE 1

GlycoProfiling

The expression profiles of the glycosyltransferases C1GalT1, C2GNT-L, C2GNT-M, ST6GalNAc-I, ST6GalNAc-II, ST3Gal-I, ST3Gal-II and ST6Gal-I from different human cell lines were investigated. The cell lines HEK293, LS174T, MCF-7 and SW480 were cultured in DMEM, while T47D, ZR75-1, NM-wt and KG1 were cultured in RPMI 1640. Both media were supplemented with 10% fetal bovine serum and 2 mM glutamine. All cells were grown at 37° C. in a humidified atmosphere of 6% $CO_2$. Cells were harvested and disrupted using standard techniques known to those skilled in the art. RNA was extracted using guanidine thiocyanate-phenol-chloroform and treated with RNase-free DNase. RNA yield was determined spectrophotometrically.

mRNA expression analysis was performed as follows: 5 g of total cellular RNA were reverse transcribed by Moloney murine leukemia virus reverse transcriptase with random nucleotide hexamers. The RT mix includes reverse transcriptase, mRNA template, primers, buffer and dNTP's. Expression of the beta-actin housekeeping gene was used to determine cDNA yield and integrity and to check for possible contamination with genomic DNA. To this end, an intron-spanning beta-actin-specific primer set was designed: beta-actin forward primer SEQ ID NO: 4,5'-GGC ATC GTG ATG GAC TCC G-3' and beta-actin reverse primer SEQ ID NO: 5,5'-GCT GGA AGG TGG ACA GCG A-3' (amplicon length, 622 bp).

The resulting cDNA strand was directly used for amplification. A forward and a reverse primer were designed to hybridize specifically to the 5'-(forward) and 3'-region (reverse) of a cDNA encoding one of the aforementioned enzymes (C1GalT1 was amplified using forward primer: SEQ ID NO: 6, GAG ATT CCA GAG ATA CCA TTG and reverse primer: SEQ ID NO: 7, CGT TCA GGT AAG GTA GGT TG (amplicon length 262); C2GNT forward: SEQ ID NO: 8, GTG CTC AGA ATG GGG CAG GAT GTC ACC TGG, reverse: SEQ ID NO: 9, TCA CTA CTA GGA TTC TCC CCA GCA AGC TCC (amplicon length 360); ST3Gal-I forward: SEQ ID NO: 10, ATG AGG TGG ACT TGT ACG GC, reverse: SEQ ID NO: 11, AAC GGC TCC AGC AAG ATG (amplicon length 375); ST3Gal-II forward: SEQ ID NO: 12, CCC TGC TCT TCA CCT ACT CG, reverse SEQ ID NO: 13, GCA TCA TCC ACC ACC TCT G (amplicon length 282); ST6Gal-I forward: SEQ ID NO: 14, AAA AAC CTT ATC CCT AGG CTG C, reverse: SEQ ID NO: 15, TGG TAG TTT TTG TGC CCA CA (amplicon length 379); ST6GalNAc-I forward: SEQ ID NO: 16, ACC ACA GCC AAG ACG CTC, reverse: SEQ ID NO: 17, AAG GGT GGT GCA AAG TGT TC (amplicon length 407); ST6GalNAc-II forward: SEQ ID NO: 18, CTG CCA GTA AA T TCA AGC TGC, reverse: SEQ ID NO: 19, TTG CTT GTG ATG MT CCA TAG G (amplicon length 184)). The PCR reaction mixture contained 1.5 l of PCR buffer [100 mM Tris-HCl (pH 8.3), 500 mM KCl], 0.8-1.0 l of 25 mM $MgCl_2$, 5 l of cDNA, 1.5 l of 2 mM deoxynucleotide triphosphates, 0.2 l of Ampli-Taq polymerase, 0.2 l of 0.25 M beta-actin primer, 0.7-0.8 l of 50 M enzyme-specific primers and $H_2O$ to a volume of 15 l. PCR run multiple temperature cycles for denaturation, annealing and elongation. Cycling conditions were 1 min at 94° C., 1 min at 59° C. and 2 min at 72° C. beta-actin was co-amplified within the same tube with 0.2 l of beta-actin primer. Each PCR reaction was performed twice.

Aliquots of PCR reaction obtained after 26 to 28 cycles were electrophoresed in 2% agarose gels and quantified via the intensity of ethidium bromide staining. For semiquantitative analysis of the RT-PCR data, the staining intensity of each cDNA-specific band was compared with the staining intensity of band corresponding to co-amplified beta-actin. The intensity of each enzyme band was correlated with the appropriate beta-actin band by calculating the ratio [(fluorescence units of the enzyme band/fluorescence units of beta-actin)×100]. The detection limit was 1 ng of double-stranded DNA. The assay was linear up to 25 ng. GlycoProfiling revealed a complete deficiency to synthesize core 2 by lack of C2GNT-L and C2GNT-M for NM-wt cells only. Other reductions in mRNA expression concerning ST6GalNAc-II to 8% and ST3Gal-I to 32% could be compensated by intact ST6GalNAc-I and ST3Gal-II (Table 1). This glycosyltransferase profile of NM-wt represented the best starting point for future GlycoEngineering and sialylation studies by using the TF epitope.

The carbohydrate determinants with special regard to sialic acid were detected in the aforementioned human cell lines by means of flow cytometry applying several monoclonal antibodies and lectins.

Cells were harvested, washed twice with PBS and allowed to recover for 1 h at 37° C. For neuraminidase treatment, cells were incubated for 30 min at 37° C. in 0.1 M imidazole buffer (pH 6.8) containing 0.1% $CaCl_2$ and 0.4% NaCl with or without *V. cholerae* neuraminidase. Cells were resuspended in staining buffer (HBSS containing 4% BSA or medium containing 10% FCS). For the examination of cell surface carbohydrate determinants different antibodies and lectins were used. For example, expression of TF was analyzed using the biotin-labeled lectins peanut agglutinin (PNA), jacalin from *Artocarpus integrifolia, Amaranthus caudatus* agglutinin (Amaranthin or ACA) and *Bauhinia purpurea* lectin (BPL), and the TF-specific monoclonal antibody A78-G/A7. PankoMab detects tumor-MUC1, A83-C/B12 is an anti-GPA antibody recognizing Glycophorin A independent of its glycosylation. Cells were incubated with lectins or antibodies for 1 h at 4° C. and washed twice with staining buffer. Binding of the antibodies was detected by the secondary Cy3-goat anti mouse IgG/IgM antibody. Binding of lectins was detected by Cy3-conjugated streptavidin. Flow cytometric analyses were performed using a Coulter Epics XL flow cytometer (Beckman Coulter, Germany). Quantitative analyses were carried out using the Expo32 software (Becton Coulter).

With the exception of ZR75-1, human cells were TF-negative. However, after treatment of cells with neuraminidase that cleaves off sialic acids cryptic TF becomes visible on many cell lines. Among the analyzed cell lines NM-wt cells were the major carrier of cryptic TF. With regard to the present invention, high amounts of original cryptic TF and released sialic acid are favored (Table 2).

EXAMPLE 2

GlycoEngineering and Characterization of Novel Clones

Random mutagenesis was performed by treating NM-wt cells with the alkylating agent ethyl methanesulfonate. Per sample NM-wt cells were washed in PBS and seeded at $10^6$ cells per ml cell culture medium supplemented with EMS (0.1 mg/ml, ethyl methanesulfonate, Sigma-Aldrich) overnight at 37° C. and 5% $CO_2$. Cells were washed and provided with fresh medium. Every second day cell vitality was determined by trypan blue staining, and cells were analyzed by immunocytochemical staining (FIG. 1A).

Subsequently, cells exposing the novel phenotype of high TF expression were selected using a TF-specific antibody. NM-wt cells were washed in B-PBS (0.5% BSA in PBS), incubated with 50 µl of supernatant of hybridoma cultures of the monoclonal antibody A78-G/A7 or PankoMab and 950 µl of B-PBS at 4° C. for 30 min. After washing the procedure was repeated with 50 µl of rat-anti-mouse-IgM-antibody or rat-anti-mouse-IgG-antibody conjugated with MicroBeads (Miltenyi Biotec, Köln, Germany). After washing the magnetically labeled TF-positive cells were separated by two successive columns provided by Miltenyi Biotec (Köln, Germany) as described in the manufacturers manual. Following nine days of cultivation, the isolation procedure was repeated in total three times. FACS analysis (flow cytometry) started with antibody staining: About $3 \times 10^5$ cells were incubated at 4° C. for 1.5 h with primary monoclonal antibody (hybridoma culture supernatants of A78-G/A7 (IgM), PankoMab (IgG1), all diluted 1:2 in cell culture medium) followed by the secondary Cy3-conjugated goat anti-mouse IgM/IgG antibody 1:200 diluted in PBS, at 4° C. for 30 min and were washed again. Resuspended cells (200 µl PBS) were investigated by flow cytometry. Quantitative analyses were carried out using the Expo32 software (Becton Coulter) with following parameter for antibody labeled cells: forward scatter (FS): 26 V, gain 1, sideward scatter (SS): 807 V, gain 5, FL2: 740 V, gain 1, and following parameter for lectin labeled cells: FS: 26 V, gain 1, SS: 807 V, gain 5, FL1:740 V, gain 1.

After three rounds of isolation a cell population of 93% TF-positive cells was received. However, the percentage of TF-positive cells decreased over time reaching a bottom level of about 20% TF-positive cells during a period of 14 days following the isolation procedure. For stable expression of the TF-positive phenotype, cells were isolated for a forth time and finally, the isolated TF-positive cells were cloned thereafter by limited dilution in 96-well plates (1 cell/100 µl). Among thirty cell clones that were obtained, thirteen cell clones expressed high amounts of the TF antigen and from these eight cell clones displayed a homogenous TF expression on the cell surface of the whole cell population (FIG. 1A). These cell clones stably express the TF antigen until now (about 30 month). Analysis by flow cytometry revealed approximately a 31-fold increase of the TF expression level for NM-F9 cells reflecting the strong expression of TF on this clone, also demonstrated by a subtractive mean in FACS analysis of about 35 which was chosen for further characterization. The necessity for cloning in order to obtain a stable TF-positive cell population is due to a higher proliferation rate of TF-negative cells which hence overgrow TF-positive clones over time, e.g. NM-F9 has a slower doubling rate than NM-wt cells.

Furthermore, a MUC1 selection was performed in accordance to the TF selection, but with the exception that PankoMab and rat-anti-mouse-IgG-antibody conjugated with MicroBeads (Miltenyi Biotec, Köln, Germany) were used. For the generation of a TF-positive clone which expresses more of the tumor-specific MUC1 epitope TA-MUC1, NM-F9 cells were treated, selected and single cell cloned as described above using PankoMab for selection. The stable clone NM-D4 was selected for further characterization due to its increased PankoMab staining in flow cytometry.

NM-F9 and NM-D4 could be adapted to serum-free media by passaging into media with successive lower concentrations of fetal calf serum (FCS).

Figure 2:
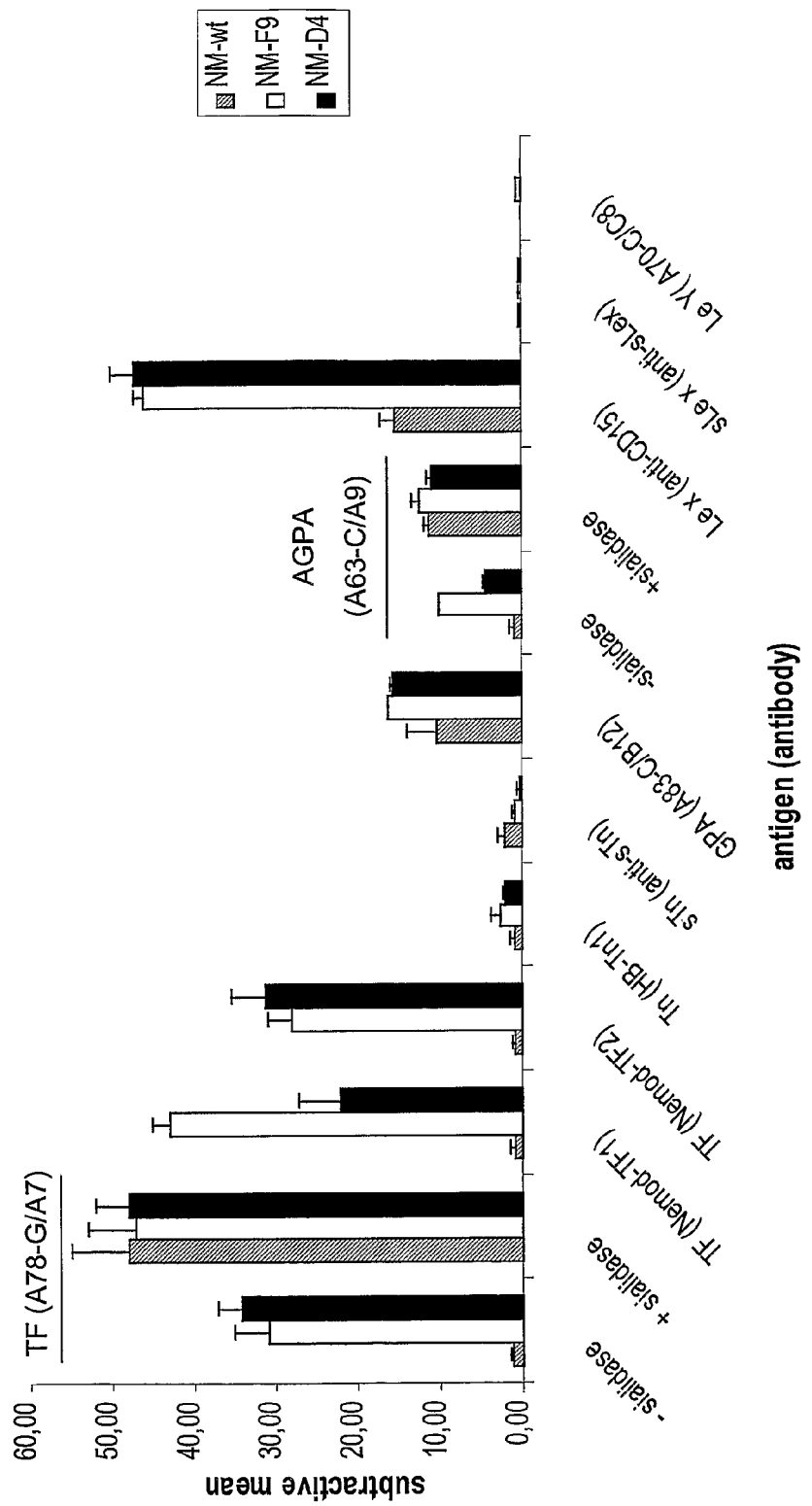
FIG. 2: Expression of TF, sTF, Tn, sTn, glycophorin A (GPA), asiologlycophorin A (AGPA), Le$^x$, sLe$^x$, and Le$^y$ by NM-wt cells, and derivatives NM-F9 and NM-D4. Cells were analysed by flow cytometry. Additionally cells were sialidase treated and analyzed for AGPA (A63-C/A9) and TF (A78-G/A7) expression.

NM-F9 and NM-D4 were characterized in detail for their carbohydrate determinants and transferase expression. The sialylation degree of assessable membrane glycoconjugates was determined by flow cytometry applying the TF-specific antibody A78-G/A7 as described in example 1, and several lectins, e.g. the terminal beta-Gal recognizing PNA, the sialic acid-specific *Sambucus nigra* lectin (SNA), or others like *Maackia amurensis* lectin I (MAA) and *Ulex europaeus* agglutinin I (UEA I). After washing twice with PBS and once with HBSS with 4% BSA (Hanks' Balanced Salt), cells were incubated with FITC-conjugated PNA (1:400), FITC-conjugated SNA (1:50), FITC-conjugated MAA (1:50) or FITC-conjugated UEAI in HBSS/4% BSA at 4° C. for 1 h. After washing cell pellets were resuspended in 200 µl of HBSS/4% BSA for analysis. Quantitative analyses were carried out using the Expo32 software (Beckman Coulter) with following parameter for antibody labeled cells: forward scatter (FS): 26 V, gain 1, sideward scatter (SS): 807 V, gain 5, FL2: 740 V, gain 1, and following parameter for lectin labeled cells: FS: 26 V, gain 1, SS: 807 V, gain 5, FL1:740 V, gain 1 (FIGS. 2 and 3A).

Figure 1B:
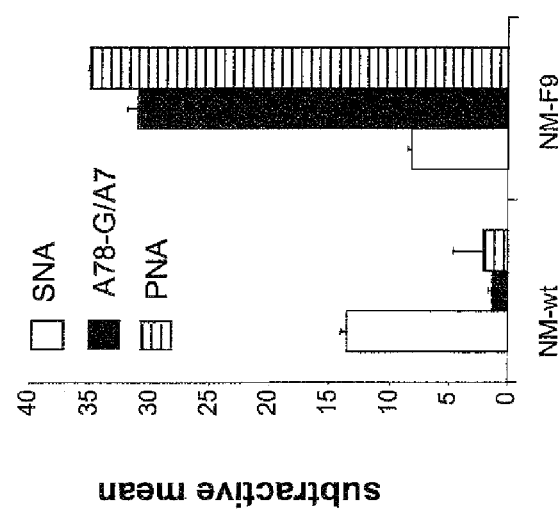
Figure 1C:
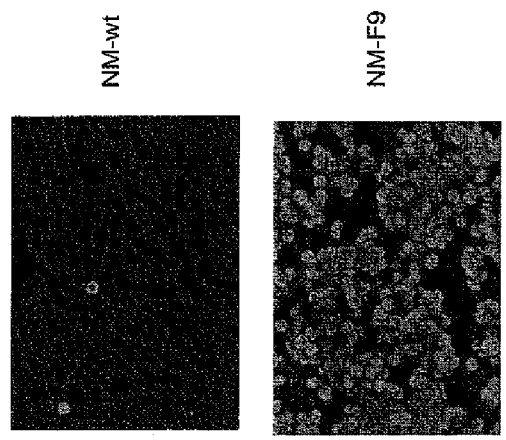

Whereas the cryptic TF of wild type cells prevented binding of A78-G/A7 and PNA, the exposed one of the derivatives NM-F9 and NM-D4 enhanced recognition by a factor of 30 to 75 depending on the detecting agent used. The result was qualitatively confirmed by the reverse affinity of SNA (FIG. 1B). In addition, the amount of membrane-bound sialic acid was quantified. Briefly, cells were harvested, washed once with PBS, and lysed in lysis buffer (50 mM Tris/HCl pH 8, 150 mM NaCl, 0.5% Nonidet P40, 1 mM EDTA, 200 µg/ml phenylmethylsulfonyl fluoride) in combination with needle sheering. The crude membrane fraction was pelleted by centrifugation at 40.000×g for 20 min. The pellet was washed twice with water and lyophilized. Supernatant was used for enzyme activity measurements (see example 3). Protein concentration was determined with the Roti-Quant-Kit (Roth, Germany). The content of membrane glycoconjugate-bound sialic acid was determined by hydrolyzing the pellet for 1 hour with 2 M acetic acid at 80° C. and released sialic acids were determined by the thiobarbituric acid method (Aminoff, Biochem. J. 81, 384-392, 1961). Membrane-bound sialic acid in NM-F9 and NM-D4 cells compared to wild type cells is reduced to about one third (FIG. 1C, 3B).

EXAMPLE 3

Analysis of the Genetic Defect of NM-F9 Cells

Figure 4B:
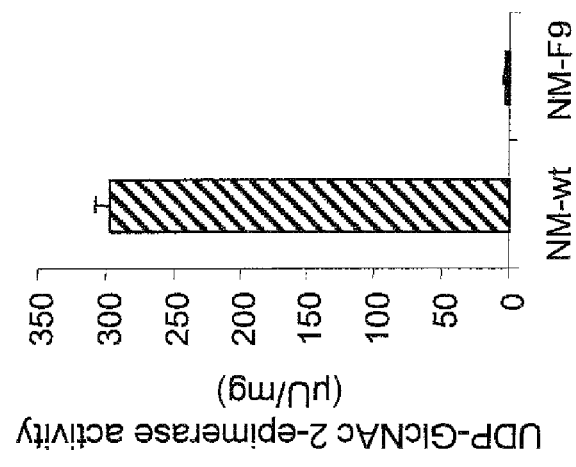
FIGS. 4A-B: Analysis of the genetic defect of NM-F9 cells by (FIG. 1A) mRNA expression analysis and (FIG. 1B) enzyme activity analysis. mRNA expression analysis comprises isolation of RNA, RT-PCR using UDP-GlcNAc-2-epimerase specific primers and gel electrophoresis. Actin was run as control. Enzyme activity determination is based on measurement of in vitro conversion of $^{14}$C-UDP-N-acetylglucosamine to $^{14}$C—N-acetylmannosamine. The mRNA of the UDP-GlcNAc-2-epimerase could not be detected, and the absent enzyme activity confirmed the genetic defect of the epimerase.
Figure 4A:
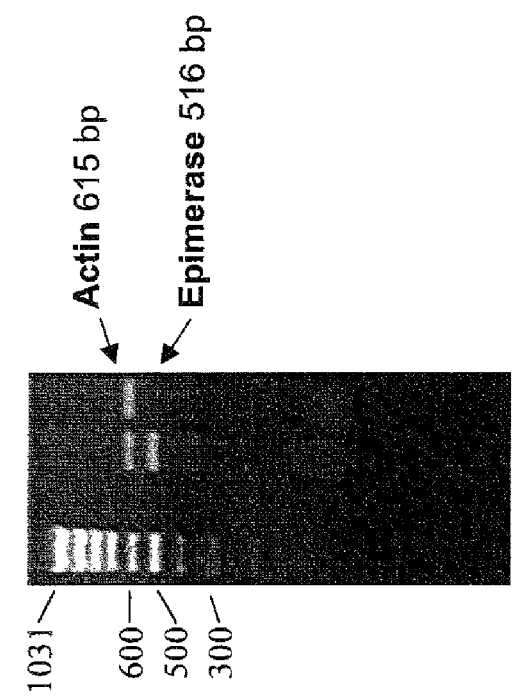

TF exposure of NM-F9 cells was expected to need a defect in several sialyltransferases, in the sugar nucleotide biosynthesis pathway or transporters. mRNA expression analysis of different enzymes was performed as described in example 1, whereby gel bands belonging to NM-F9 enzymes were compared to those of NM-wt, and revealed a total lack of UDP-GlcNAc-2-epimerase mRNA (FIG. 4A). Enzyme activity of UDP-GlcNAc-2-epimerase in NM-wt and NM-F9 cells was determined in cell supernatant (see example 2) by measuring conversion of $^{14}$C-UDP-N-acetylglucosamine to $^{14}$C—N-acetylmannosamine using paper chromatography. 1 U corresponds to synthesis of 1 µmol ManNAc per min at 37° C. UDP-GlcNAc-2-epimerase activity was completely dropped in NM-F9 from original 300 µU/mg in NM-wt cells (FIG. 4B).

Figure 5B:
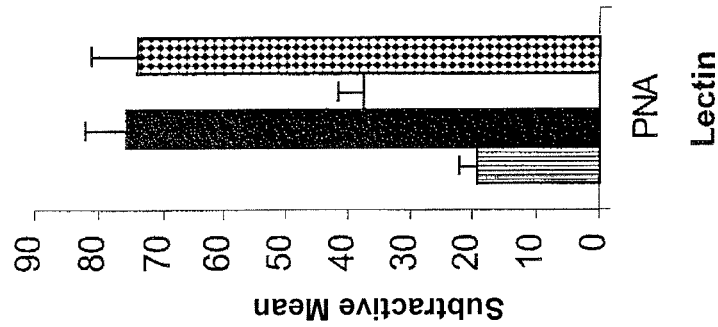
FIGS. 5A-B: Reconstitution of sialylation by metabolic complementation. NM-F9 and NM-wt cells were cultivated in serum containing none or 50 mM of ManNAc or of GlcNAc, respectively, for four days. Monoclonal antibodies A78-G/A7 (anti-TF) and A63-C/A9 (anti-AGPA), and lectins SNA, MAA (FIG. 5A) and PNA (FIG. 5B) were used in flow cytometric measurements. Supplement of ManNAc led to reconstitution of sialylation and to the disappearance of TF. Due to the UDP-GlcNAc-2-epimerase defect, GlcNAc could not be metabolized.
Figure 5A:
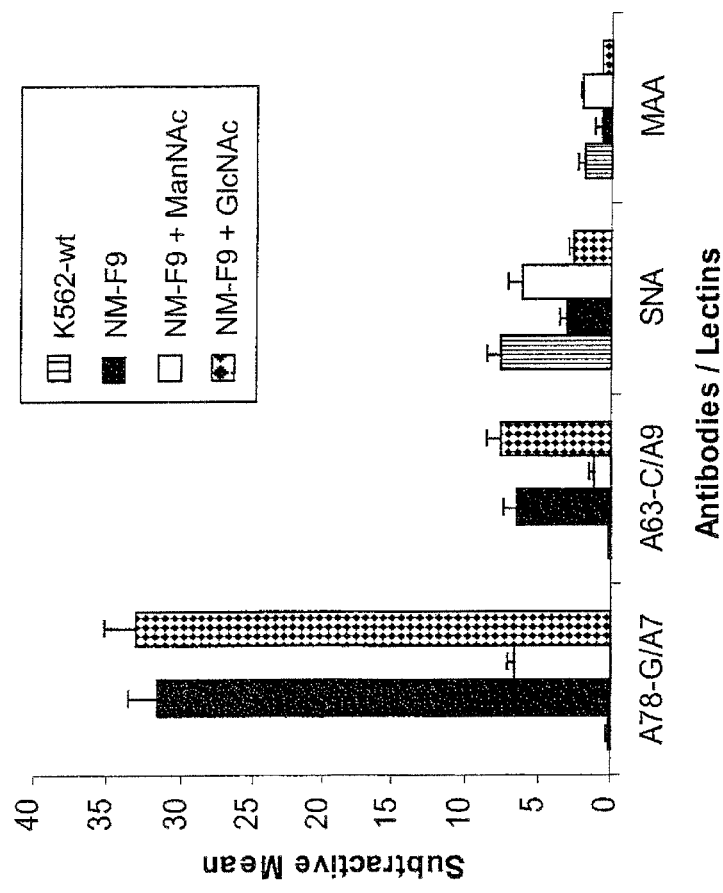

In order to investigate the capability of NM-F9 cells to reconstitute sialylation, medium was supplemented with 50 mM ManNAc. After cultivation for four days the remaining sialic acid free glycotopes were detected by means of flow cytometry applying the monoclonal antibodies A78-G/A7 and A63-C/A9, and the lectins PNA, SNA, and MAA, as already described. The metabolic complementation by feeding ManNAc led to about 50% (PNA) to 80% (A78-G/A7) of cryptic membrane glycoconjugate TF depending on the detecting agent. Due to the UDP-GlcNAc-2-epimerase defect, the control GlcNAc could not be metabolized by NM-F9 cells (FIG. 5A-B).

Figure 6:
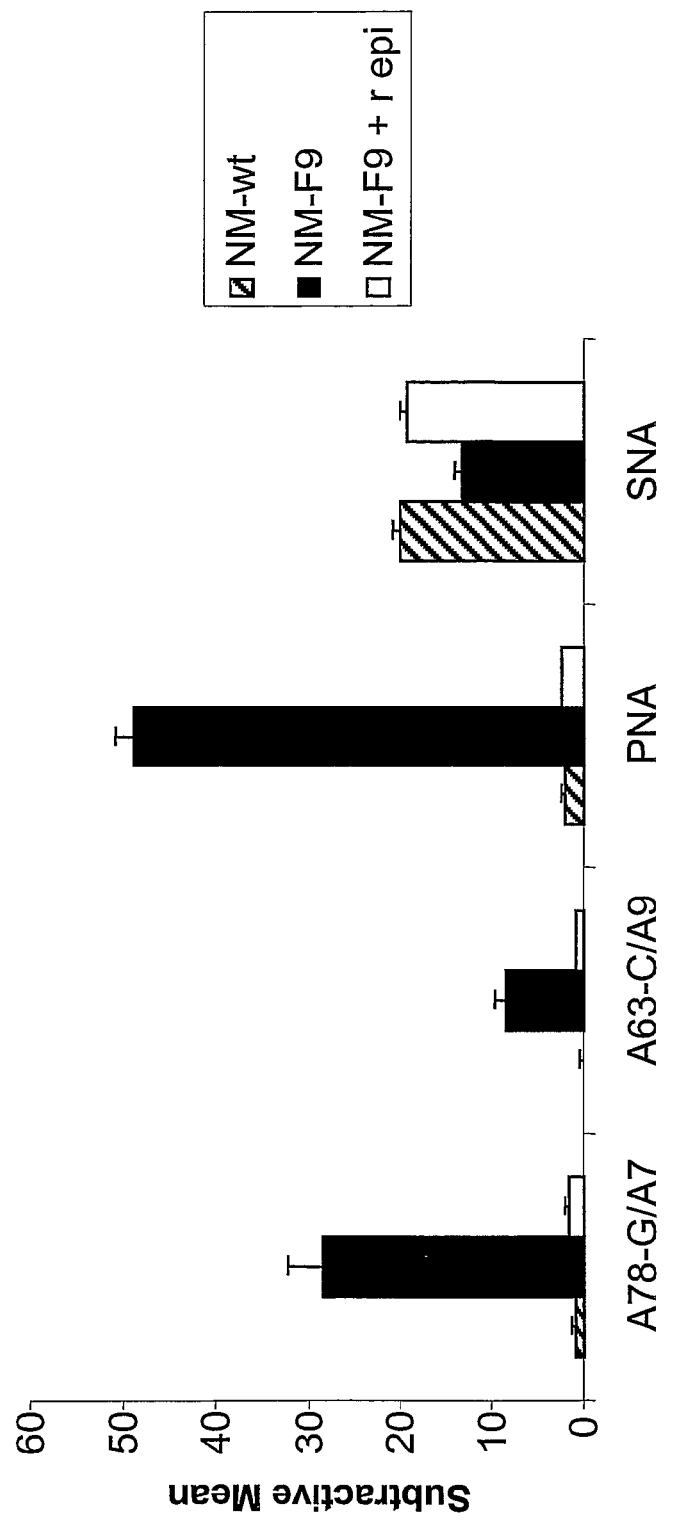
FIG. 6: Reconstitution of sialylation by genetic complementation. NM-F9 cells were stably transfected with the epimerase encoding construct pcDNA3.1Zeo(−)/2Epi. Monoclonal antibodies A78-G/A7 and A63-C/A9, and lectins SNA and PNA were used in flow cytometric measurements. Sialylation was completely restored.

In addition, the reconstitution of sialylation by genetic complementation was investigated.
UDP-GlcNAc-2-epimerase cDNA was cloned into the vector pcDNA3.1. NM-F9 cells were stably transfected with the epimerase encoding construct pcDNA3.1Zeo(−)/2Epi using the SuperFect reagent. Cells were grown to 40% confluence. 5 µg of DNA were dissolved in 150 ml of DMEM and mixed with 30 µl of SuperFect. After a 10-min incubation at room temperature this solution was added to the cells. After 3 h the medium was removed, and the cells were washed three times with PBS and incubated with fresh growth medium. After a incubation period of 48 h growth medium was replaced again with medium containing 700 µg/ml G418 or 750 µg/ml zeocin. Resistant clones were maintained continuously in growth medium containing 400 µg/ml G418 or 250 µg/ml zeocin and analyzed by flow cytometry. Monoclonal antibodies A78-G/A7 and A63-C/A9, and lectins PNA and SNA were used to detect sialic acid free glycotopes. Sialylation degree was completely restored (FIG. 6).

EXAMPLE 4

Recombinant Expression of Secreted Glycoproteins in NM-F9 Cells

NM-F9 cells stably expressing the recombinant human growth factor rhGM-CSF were generated by transfection of the cells with the expression vector pGT60hGM-CSF (Invivogen, USA) by using the electroporation. For electroporation $10^6$ cells were harvested, washed, resuspended in 400 µl of hypoosmolar buffer (Eppendorf, Germany) and incubated for 15 min at room temperature. Thereafter, the cell suspension was mixed with 8 µg of the plasmid DNA and transferred into an electroporation cuvette with an 2 mm gap (Eppendorf). The electroporation was performed in a Multiporator (Eppendorf) by using a voltage of 340 V and a time of 5 µsec. After 1-2 days of recovery from electroporation in culture medium (10% fcs, 1% glutamine in RPMI 1640, Biochrom) stably transfected cells were selected by using 100 µg/ml of the antibiotic hygromycin B and cloned by the limited dilution technique. About 4 weeks later the supernatant of several cell clones were analyzed for the presence of secreted rhGM-CSF by using a GM-CSF specific ELISA (Becton-Dickenson, USA) which can be used to quantify the GM-CSF content. One cell clone with the highest secretion rate of rhGM-CSF was selected for further experiments.

Figure 7:
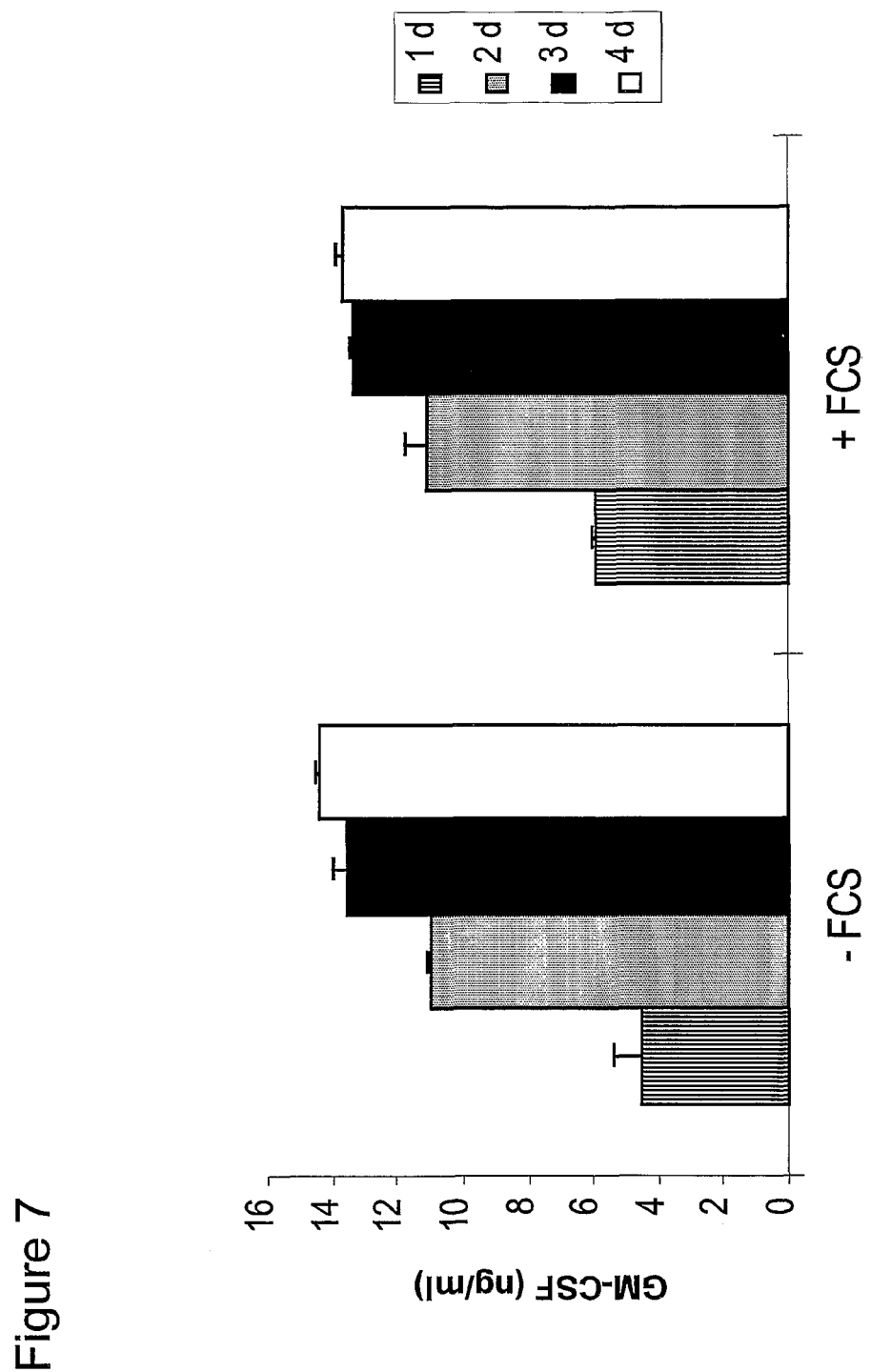
FIG. 7: rhGM-CSF expression in NM-F9. NM-F9 cells stably transfected with the human GM-CSF expression vector were cloned and cultured in media supplemented with and without FCS. GM-CSF concentration in the supernatant were determined after 1 day (1 d), 2 (2 d), 3 (3 d) and 4 days (4 d) by ELISA. After 4 days, 14 ng/ml GM-CSF per $10^5$ NM-F9 cells were secreted.

In a first experiment, about $10^5$ NM-F9 cells stably expressing GM-CSF were cultivated in culture medium (see above) with and without fetal calf serum (fcs). After 1, 2, 3 and 4 days of cultivation without changing the medium the amount of secreted rhGM-CSF which accumulated over the time was determined by using the GM-CSF specific ELISA. About 14 ng GM-CSF was released by $10^5$ cells in 4 days independently whether cultured with or without fcs (FIG. 7). The secretion rate after 1 day was slightly higher (about 6 ng/ml) when cultivated with fcs compared to the culture without fcs (about 4 ng/ml).

Figure 8:
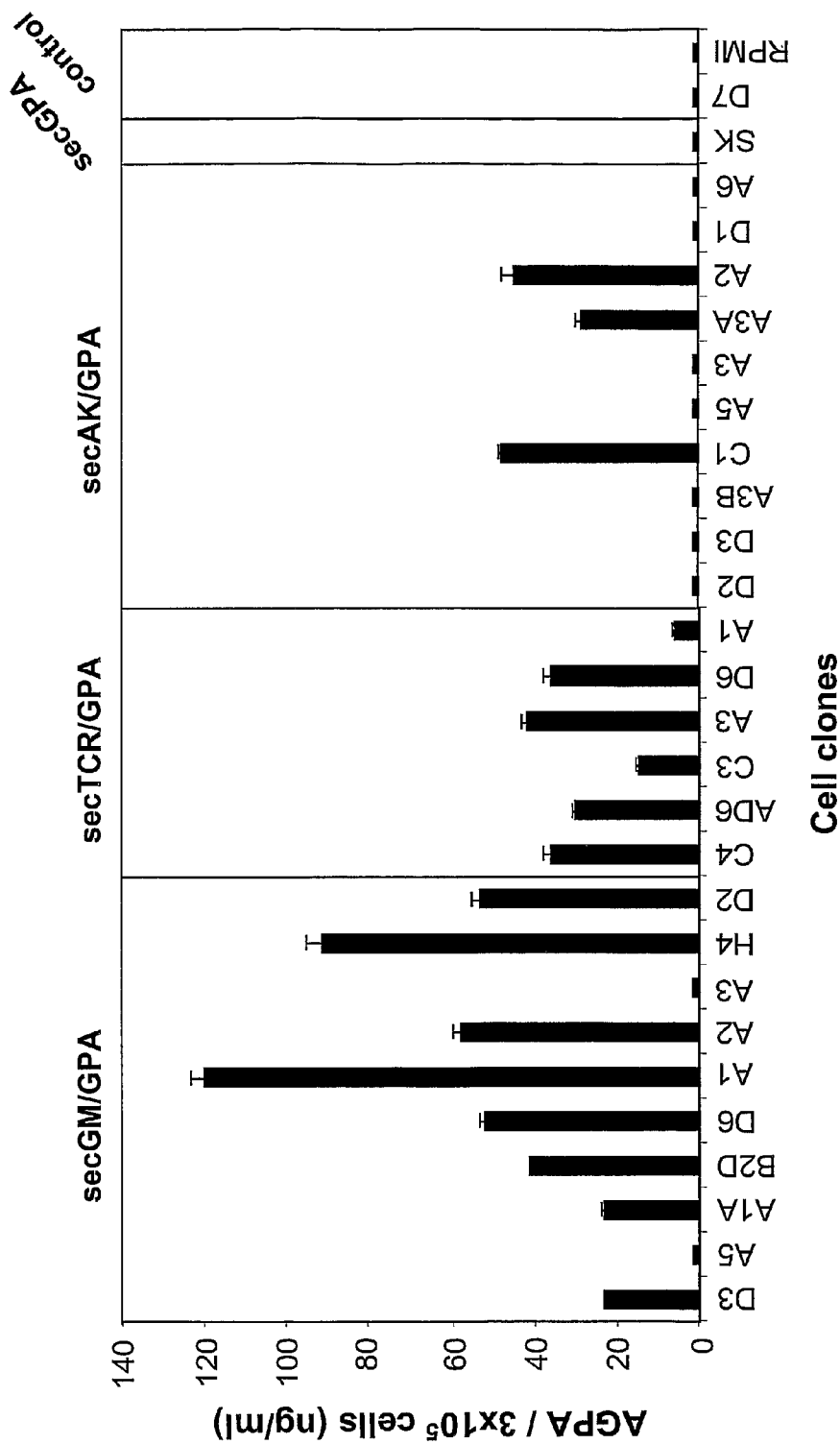
FIG. 8: Expression of recombinantly expressed secretory AGPA by NM-F9 cells using different secretory signal peptides. For expression of a secretory AGPA four expression vectors were constructed containing the signal peptide of GM-CSF (secGM/GPA), of the T cell receptor (secTCR/GPA), of the antibody light chain [] (secAK/GPA) and with the endogenous signal peptide (secGPA). Secretory AGPA was detected in cell supernatant by sandwich ELISA using A83-C/B12 (anti-GPA) as catcher and A63-C/A9 as detector.

The human membrane protein Glycophorin A (GPA) was recombinantly expressed in NM-F9 cells as secretory Asialoglycophorin A using the expression vector construct secGPA. SecGPA contains the cDNA encoding for the N-terminal 91 amino acids (aa) of GPA without the transmembrane domain and the cytoplasmic tail. This cDNA was subcloned into the eukaryotic expression vectors pcDNA5/FRT/V5-His-TOPO and/or pcDNA3.1/myc-His C (both Invitrogen). Furthermore, NM-F9 cells were used to express recombinant fusion proteins of the secretory AGPA protein where the endogenous signal peptide was replaced by heterologous human signal peptides. Therefore, using molecular biological methods that are known to skilled persons the cDNAs secGM/GPA, secTCR/GPA and secAK/GPA were constructed where in place of the 19 N-terminal aa encoding cDNA the heterologous cDNA was integrated encoding for the signal peptides from GM-CSF (SEQ ID NO:1, MWLQS-LLLLGTVACSIS, secGM/GPA), from the T cell receptor (SEQ ID NO:2, MACPGFLWALVISTCLEFSMA, secTCR/GPA) or from the antibody k light chain (SEQ ID NO:3, METDTLLLWVLLLWVPPGSTGD, secAK/GPA). The latter two signal peptides are already known to skilled persons for use as heterologous signal peptides to increase the secretory expression of any gene product. In case of secGM/GPA an additional alanine is expressed just between the signal peptide and the GPA encoding backbone. The three cDNA constructs were subcloned into the expression vectors mentioned above and the nucleotide sequences were confirmed. Each of the resulting expression vectors was used for the generation of stably transfected NM-F9 cells by using the procedure described above, electroporation, selection with hygromycin B and single cell cloning. In case of usage of the expression vector pcDNA5/FRT/V5-His-TOPO, genetically modified NM-F9 cells, which contained a lacZeo DNA cassette (Invitrogen) framed by two FRT recombinase recognition sites, were co-transfected with pcDNA5/FRT/V5-His-TOPO and the recombinase expression vector pOG44 (Invitrogen). secGM/GPA-, secTCR/GPA-, secAK/GPA- or secGPA-expressing cell clones were screened for secretion of a secretory AGPA that is released into the cell culture medium by a sandwich ELISA using the A83-CB12 antibody to catch any GPA out of the cell culture supernatant and the A63-C/A9 antibody that recognizes the TF-antigen localized on the extracellular domain. FIG. 8 shows that the cell clones that produced the highest amounts of secretory AGPA (up to 40 ng per ml and per $10^5$ cells) were generated with the secGM/GPA-construct. Using the other constructs maximally 13 ng secretory AGPA per ml and per $10^5$ cells could be detected. Moreover, the number of cell clones that produced the secretory AGPA was significantly higher when the secGM/GPA-construct was used as expression vector (FIG. 8).

EXAMPLE 5

Differential Sialylation by Metabolic Complementation

Figure 9:
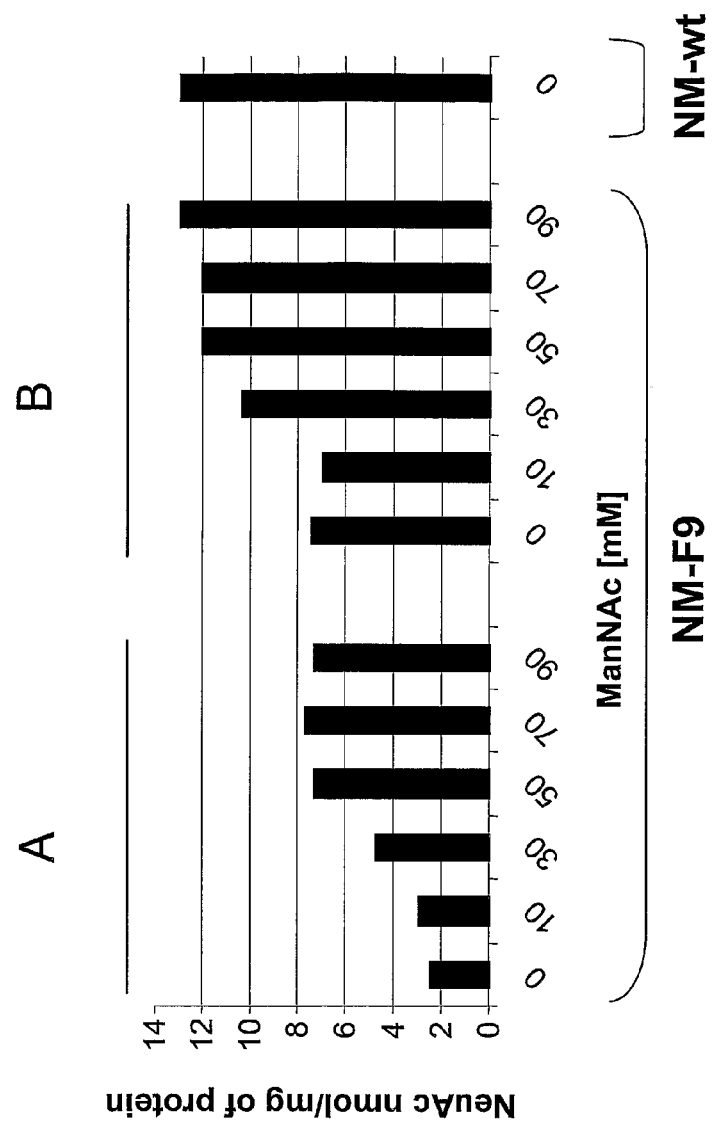
FIG. 9: Differential sialylation of membrane glycoconjugates by metabolic engineering. NM-F9 cells were cultured for four days in serum-free media (A) or in media containing fcs (B) supplemented with different concentrations of ManNAc. The amount of membrane glycoconjugate-bound sialic acid was determined by the thiobarbituric acid method of the cellular membrane fraction. For comparison, NM-wt cells were also cultured for four days in fcs-containing media without ManNAc supplementation.

Referring to the partial reconstitution of sialylation obtained by metabolic complementation of NM-F9 cells with 50 mM ManNAc (FIG. 5A-B), the influence of defined amounts of sugar intermediates on sialylation was investigated in detail. NM-F9 cells were cultivated in presence of 0-90 mM ManNAc in medium with or without fcs and the degree of sialylation of the cell membrane was analyzed by thiobarbituric acid method (see example 3). It could be demonstrated that the degree of the cellular sialylation can be controlled by metabolic complementation with increasing amounts of ManNAc in absence or presence of fcs (FIG. 9). Without supplementation of ManNAc in fcs-free medium only low amounts of sialic acids were detected in the membrane fraction of NM-F9 cells. The degree of sialylation could be gradually increased with increased amounts of ManNAc added to the fcs-free medium reaching a plateau at 50 mM ManNAc. A further increase in sialylation was achieved in fcs-containing medium supplemented with 30 mM ManNAc. The highest degree of sialylation, comparably high to the original NM-wt cells, was obtained when the fcs-containing medium was supplemented with 90 mM ManNAc.

Figure 10:
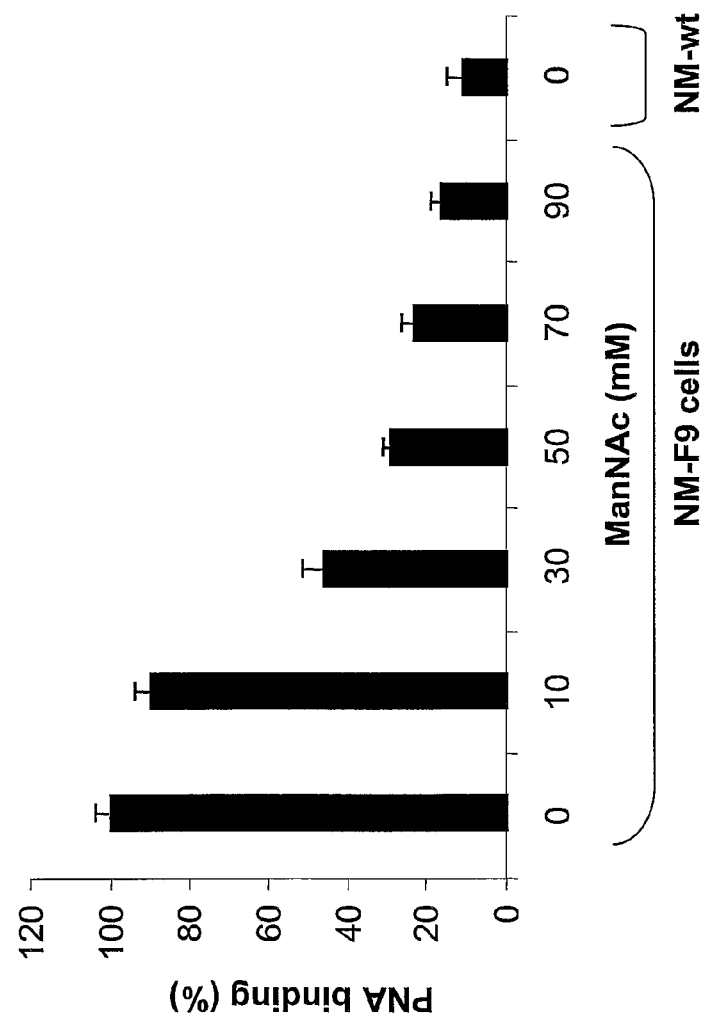
FIG. 10: Differential sialylation of membrane proteins on the cell surface by metabolic complementation. NM-F9 cells were cultured for four days in FCS-free media supplemented with different concentrations of ManNAc. For comparison, NM-wt cells were also cultured for four days in FCS-free medium without ManNAc supplementation. The flow cytometry analysis was performed with the lectin PNA which recognizes the sialic acid-free TF epitope.

Differential sialylation of membrane proteins by metabolic complementation with different concentrations of ManNAc was analyzed by flow cytometry with the lectin PNA which recognizes the sialic acid-free TF epitope and therefore inversely correlates with the degree of sialylation. It is shown that not only the amount of sialic acids in the cell membrane, but the degree of sialylation on glycoproteins in the membrane is controllable by metabolic complementation with different amounts of ManNAc (FIG. 10). An gradually increasing degree of sialylation was observed with increasing amounts of ManNAc present in the medium. With 90 mM ManNAc the sialylation degree of glycoproteins in NM-F9 cells was almost as high as in NM-wt cells.

Figure 11:
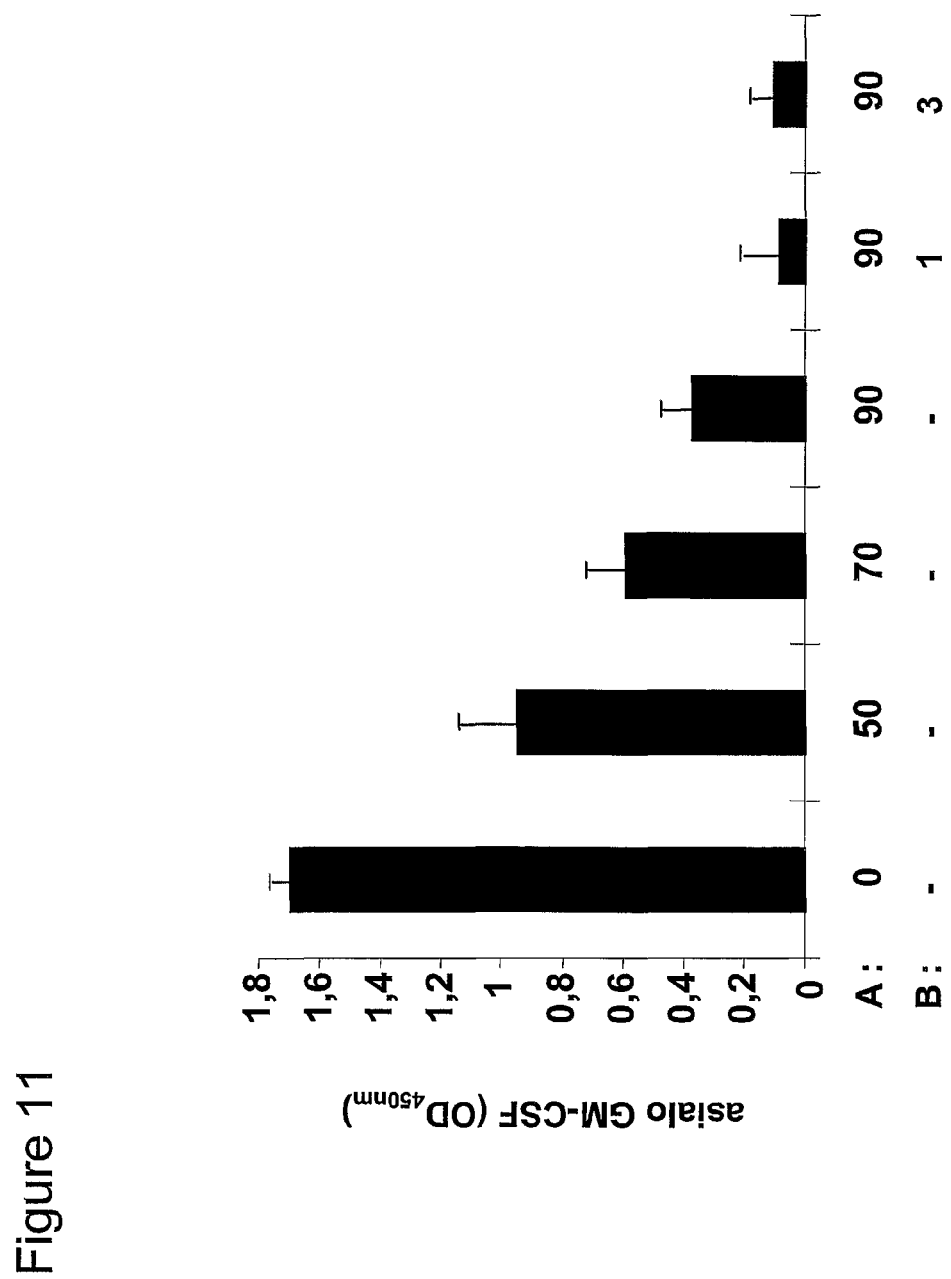
FIG. 11: Differential sialylation of secreted rhGM-CSF by metabolic complementation. rhGM-CSF producing cells were cultured for four days in serum-free media supplemented with (A) different concentrations of ManNAc (0, 50, 70 or 90 mM) and (B) −/+1 or 3 mg/ml sialoglycoprotein fetuin. Sialic acid-free rhGM-CSF was determined by ELISA. Firstly, concentration of rhGM-CSF in supernatant was determined and then adjusted to 100 ng per milliliter of NM-F9 cell culture. Secondly, for detection of sialic acid-free rhGM-CSF anti-human GM-CSF monoclonal antibody was used for catching rhGM-CSF and sialic acid-free N- and O-glycans were detected by PNA

Finally, it was tested whether also the degree of sialylation of a secretory protein, here rhGM-CSF, is controllable by metabolic supplementation with ManNAc and serum proteins. NM-F9 cells stably transfected with the rhGM-CSF expression vector (see example 4) were again cultivated with increasing amounts of 0-90 mM ManNAc and additionally with 90 mM ManNac in presence of 1 and 3 mg/ml of the sialoglycoprotein fetuin. After four days the concentrations of rhGM-CSF in the resulting cell culture supernatants were determined by ELISA (see example 4) and then adjusted to 100 ng per milliliter cell culture medium. To determine the degree of sialic acid-free rhGM-CSF a sandwich ELISA was established. Briefly, the anti-human GM-CSF monoclonal antibody of the GM-CSF specific ELISA (Becton-Dickenson) was used for catching rhGM-CSF and therefore coated to microtiter plates at dilution of 1:250 in PBS over night at 4° C. After washing in PBS/0.05% Tween 20 and blocking with 10% fcs in PBS, 100 µl of the cell culture supernatants were added to the microtiter plate and incubated for 2 h at room temperature. The sialic acid-free O-glycans were detected with biotinylated PNA (5-10 µg/ml) and peroxidase-linked streptavidin (diluted 1:250). It is demonstrated that also a secreted recombinant glycoprotein, such as rhGM-CSF, could be differential sialylated by supplementation of NM-F9 cells with increasing amounts of ManNAc (FIG. 11). The highest degree of sialylation is achieved by the addition of 1 mg/ml fetuin to 90 mM ManNAc. Addition of 3 mg/ml fetuin to 90 mM ManNAc does not result in a further increase in sialylation.

EXAMPLE 6

Identification of Highly Active Human GM-CSF by Determination of the Activity of Different Sialylation Forms To evaluate the activity of such different sialylated proteins, the ability of GM-CSF to stimulate proliferation was selected. NM-F9 cells expressing rhGM-CSF (see example 4 and 5) were cultured in different preparations containing serum-free medium supplemented with none, 30, 50, 70, and 90 mM ManNAc, and 90 mM ManNAc with 1 mg/ml of fetuin. Sialylation was detected as already described within example 5. TF-1 cells or the monocytic, dendritic cell line NemodDC, both dependent on GM-CSF in their proliferation rate, were incubated with cell supernatant adjusted to 5 ng/ml of different sialylated rhGM-CSF for 48 h or 24 h, respectively. Cell proliferation was determined by BrdU-proliferation assay according to manufacturers protocol (Roche Diagnostik GmbH, Mannheim, Germany). After fixing, cells were incubated with POD-labeled anti-BrdU-antibody. The subsequent staining reaction was stopped by 1 M sulfuric acid and detected by spectrophotometry at an optical density of 450 nm (ref. 690 nm). NM-F9 supernatant without GM-CSF was used as negative control. Commercial Leukine® of Schering AG and Leukomax® of Schering-Plough which are non-sialylated rhGM-CSF forms expressed in yeast and *E. coli*, respectively, were used as benchmark.

Figure 12:
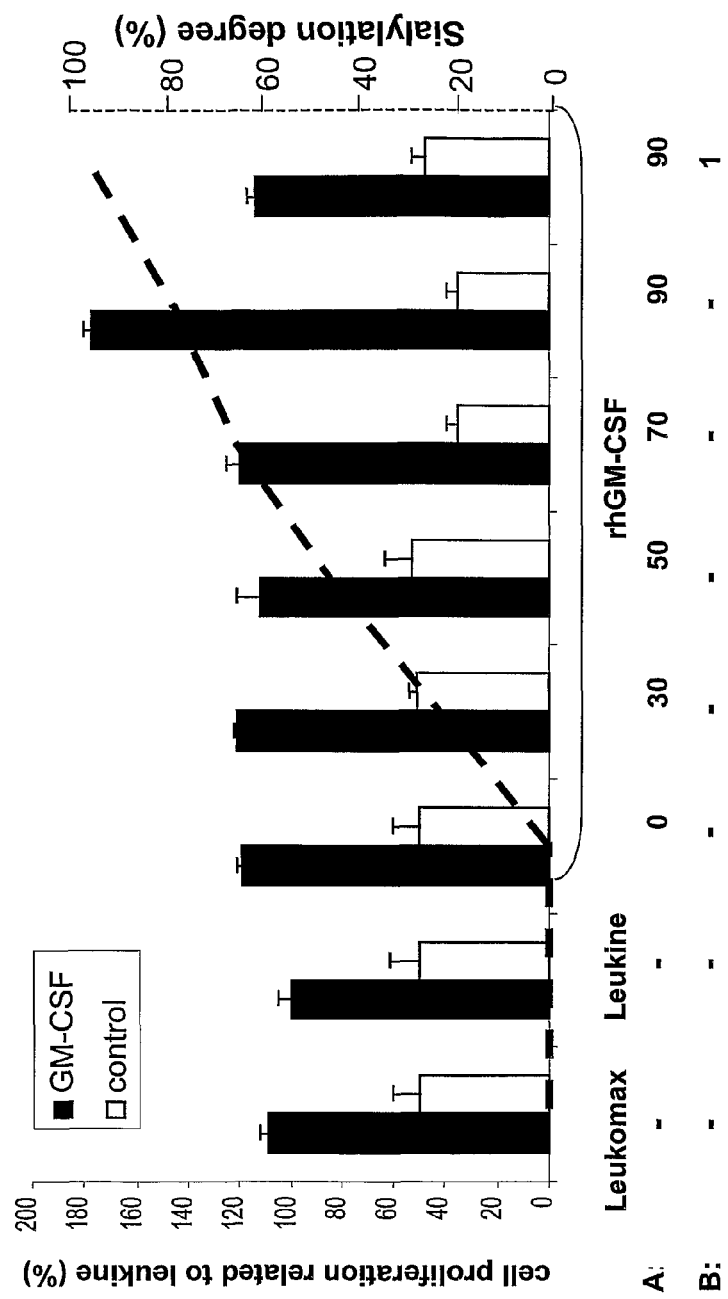
FIG. 12: Proliferation activity of differential sialylated rhGM-CSF on TF1 cells. NM-F9 cells were cultured in serum-free media supplemented with increasing ManNAc up to 90 mM (A), and 90 mM ManNAc with 1 mg/ml of defined serum sialoglycoprotein (B) for differential sialylation. TF1 cells were incubated with NM-F9 supernatant containing 5 ng/ml of different sialylated rhGM-CSF for 48 h. Leukine® (produced in yeast) and Leukomax® (produced in *E. coli*) were used as benchmark. Cell proliferation was determined by BrdU-proliferation assay using NM-F9 supernatant without GM-CSF as negative control. rhGM-CSF with a high, but not the highest sialylation degree was the most active growth factor for TF1 cell proliferation.
Figure 13:
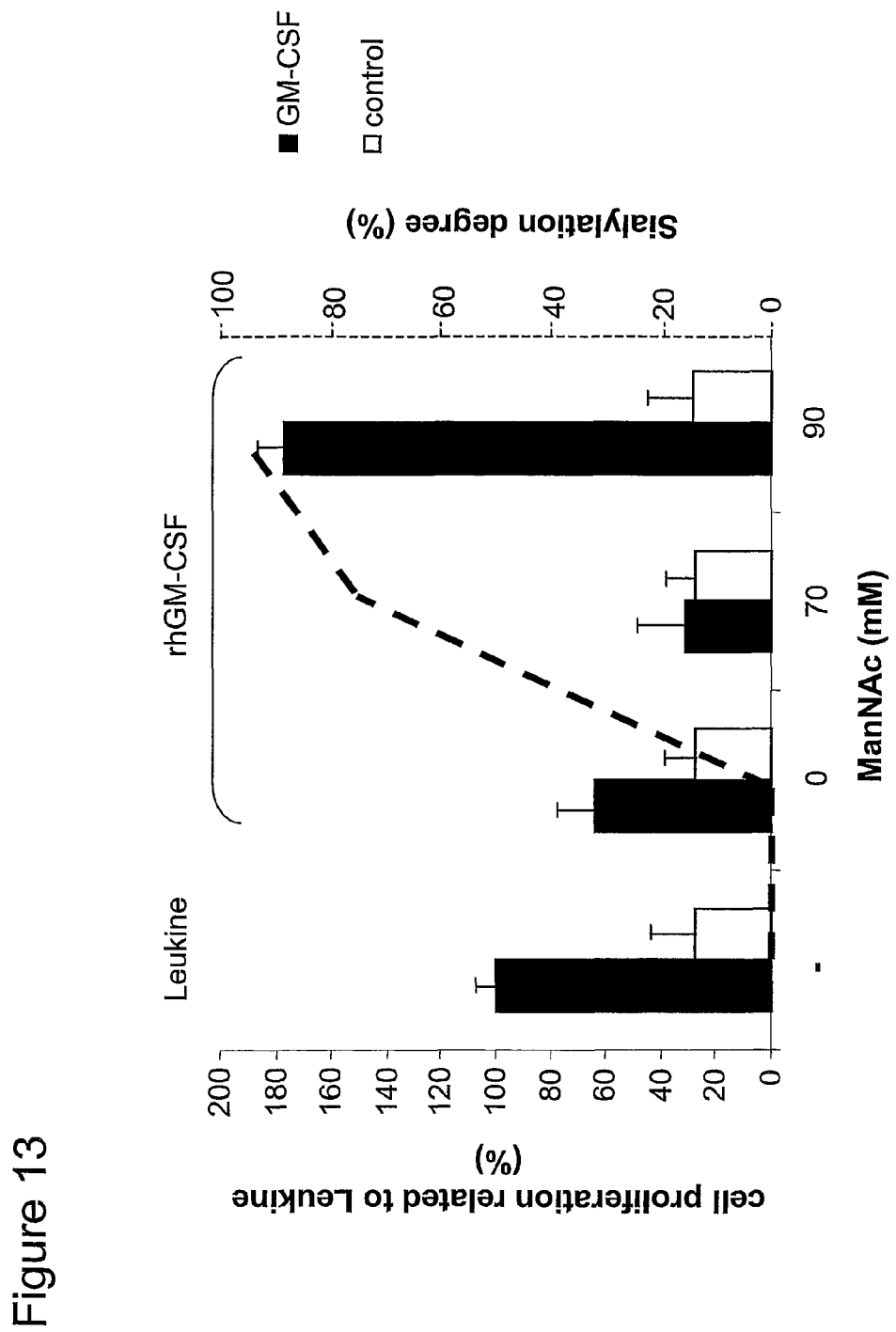
FIG. 13: Proliferation activity of differential sialylated rhGM-CSF on dendritic cells. NM-F9 cells were cultured in serum-free media supplemented with increasing ManNAc up to 90 mM for differential sialylation. NemodDC cells were incubated with NM-F9 supernatant of 5 ng/ml of different sialylated rhGM-CSF for 24 h. Leukine® was used as benchmark. Cell proliferation was determined by BrdU-proliferation assay using NM-F9 supernatant without GM-CSF as negative control. Different degrees of sialylation can have positive or negative effects on a selected activity of a glycoprotein.
Figure 14:
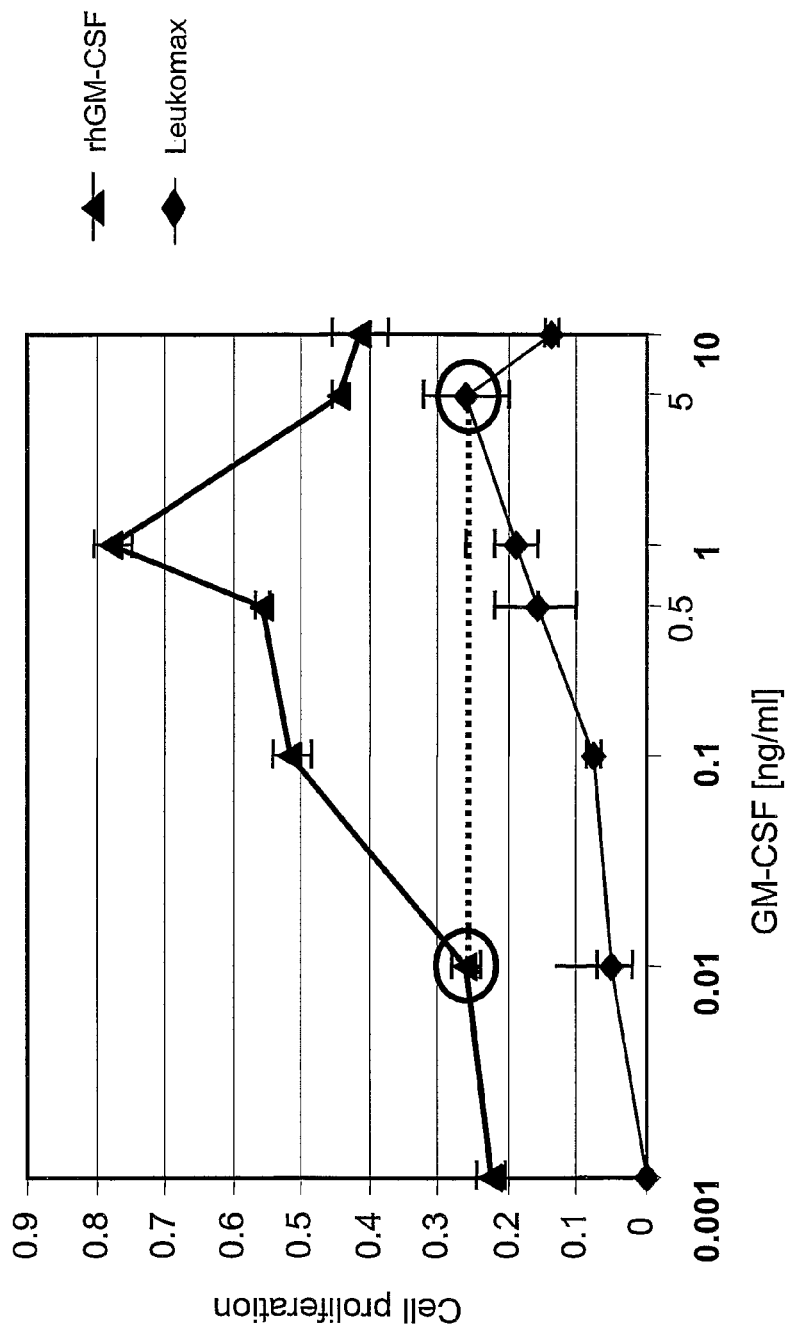
FIG. 14: Dependence of proliferation activity on rhGM-CSF concentration. NM-F9 cells were cultured in serum-free media supplemented with 90 mM ManNAc for highest activity of rhGM-CSF. TF1 cells were cultured with the supernatant of that NM-F9 cells containing different rhGM-CSF concentrations, or with different concentrations of Leukomax®, respectively, for 48 h. Cell proliferation was determined by BrdU-proliferation assay using NM-F9 supernatant without GM-CSF as negative control. In vitro activity of fully human GM-CSF is ~500 times higher than hGM-CSF expressed in *E. coli* (Leukomax) or yeast (Leukine).

Surprisingly, the cell proliferation-stimulating activity of rhGM-CSF was strongly dependent on the degree of sialylation of rhGM-CSF with one sialylation form of rhGM-CSF showing highest activity that is highly but not maximally sialylated obtained from cultures containing 90 mM ManNAc. This rhGM-CSF showed an increase in proliferation-stimulating activity of approximately 178±10% for TF-1 cells as well as for NemodDC (FIGS. 12 and 13) when compared with Leukine® (100%). The cell proliferation activity of commercially available rhGM-CSF Leukomax® and Leukine® was found to be lower than the most active sialylation form expressed in NM-F9 cells (FIG. 12). The maximal proliferation activity observed with 5 ng/ml of Leukomax® or Leukine® is achieved by 0.01 ng/ml of the optimal sialylation form from NM-F9 cells (about 500 fold less GM-CSF compared with Leukine® or Leukomax®, FIG. 14). When the activity was analyzed at the same concentrations of Leukine®, Leukomax® or the optimal sialylation form of rhGM-CSF the increase of activity was up to five-fold (FIG. 14).

Figure 15:
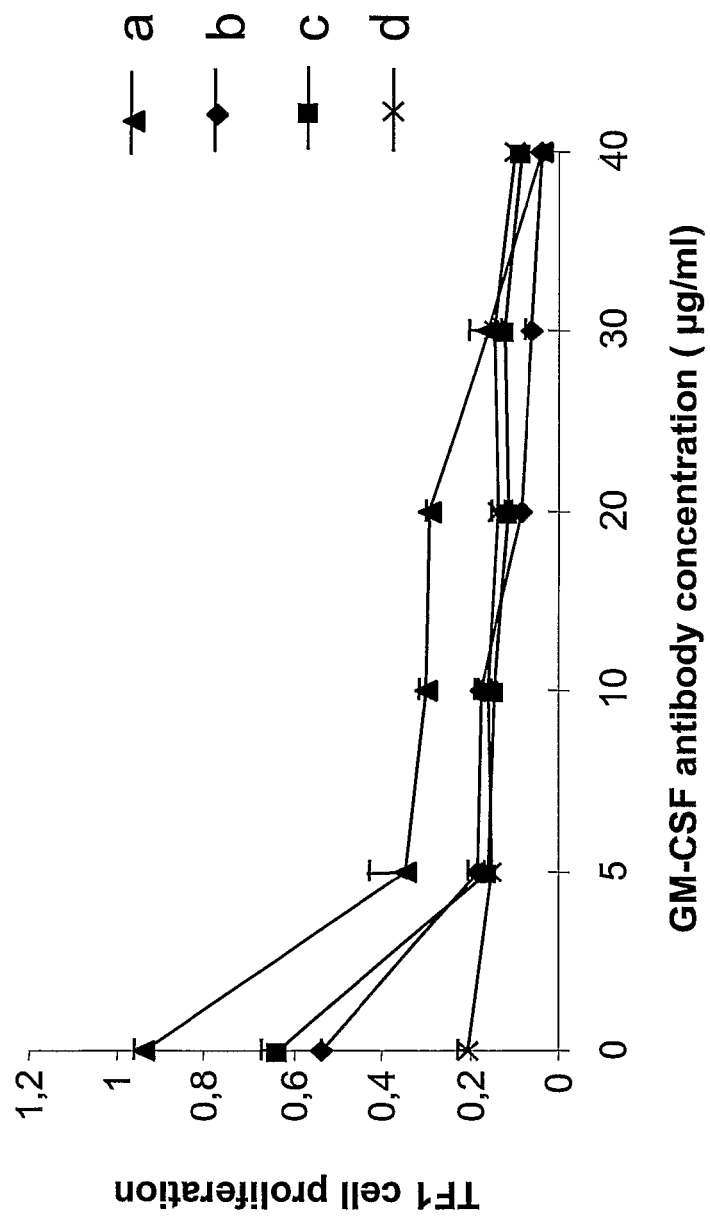
FIG. 15: Inhibition of rhGM-CSF proliferation activity. NM-F9 cells were cultured in serum-free media +/−90 mM ManNAc. TF1 cells were cultured with NM-F9 supernatant of 5 ng/ml of sialylated (a) or non-sialylated rhGM-CSF (c), or Leukine® (b), for 48 h. rhGM-CSF was successfully blocked with different concentrations of anti-human GM-CSF antibody BVD2-23 B6. Cell proliferation was determined by BrdU-proliferation assay using NM-F9 supernatant without GM-CSF as negative control (d).

If adding the anti-human GM-CSF antibody BVD2-23 B6 to the TF1 cell proliferation assay, the GM-CSF activity was specifically blocked. Already at an antibody concentration of 5 µg/ml the stimulation of TF-1 cell proliferation by Leukine® or the optimal sialylation form of rhGM-CSF was blocked by about 60% and was completely vanished at an antibody concentration of 40 µg/ml (FIG. 15).

SEQUENCE LISTING

SEQ ID NO 1: Methionine, Tryptophan, Leucine, Glutamine, Serine, Leucine, Leucine, Leucine, Leucine, Glycine, Threonine, Valine, Alanine, Cyteine, Serine, Isoleucine, Serine

---

The invention claimed is:

1. A process for the production of a highly active sialylation form of a target glycoprotein, said highly active sialylation form of said target glycoprotein having a sialylation degree that is lower than that of a reference glycoprotein, yet said highly active sialylation form of said target glycoprotein also having an activity that is higher than that of said reference glycoprotein, wherein said sialylation degree also corresponds to a determined concentration of at least one sialic acid precursor additive, said process comprising:

(a) providing a human expression cell line which harbors at least one defect in the sugar nucleotide biosynthetic pathway of sialic acids, said at least one defect being a defect in at least one enzyme selected from the group consisting of UDP-GlcNAc-2-epimerase, N-acetylmannosamine kinase, N-acetylglucosamine kinase, Neu5Ac-9-P-synthetase, Neu5Ac-9-P-phosphatase, CMP-Neu5Ac synthetase and CMP-sialic acid transporter, and said human expression cell line being transfected with a nucleic acid encoding the target glycoprotein;

(b) determining a concentration of said at least one sialic acid precursor additive that is able to reconstitute said defect by a process comprising:
   (i) expressing a plurality of different sialylation forms of said target glycoprotein by differential sialylation using different concentrations of said at least one sialic acid precursor additive;
   (ii) determining the activity of each of the different sialylation forms in comparison to the reference glycoprotein; and
   (iii) selecting said highly active sialylation form of said target glycoprotein from among the different sialylation forms expressed, and determining the concentration of the at least one sialic acid precursor additive that correlates with the expression of said highly active sialylation form of said target glycoprotein; and (c) expressing the highly active sialylation form of said target glycoprotein in said human expression cell line in a medium supplemented with the at least one sialic acid precursor additive at the concentration determined in step (b)(iii).

2. The process of claim 1, wherein the defect in the biosynthetic pathway of sialic acids is a loss-of-function of a protein involved in the sugar transportation, and wherein the protein involved in the sugar transportation is a CMP-sialic acid transporter.

3. The process of claim 1, wherein the addition of said sialic acid precursor additive results in glycoproteins with natural sialic acid modifications.

4. The process of claim 1, wherein the defect in the biosynthetic pathway of sialic acids results in a decreased or absent enzymatic activity of UDP-N-acetylglucosamine-2-epimerase.

5. The process of claim 1, wherein the glycoprotein is secreted by the cells of the expression cell line.

6. The process of claim 1, wherein the expression cell line is selected from the group consisting of NM-F9 (deposited under the accession number DSM ACC2606), and NM-D4 (deposited under the accession number DSM ACC2605).

7. The process of claim 1, wherein the glycoprotein is selected from the group consisting of Glycophorin A, erythropoietin (EPO), granulocyte colony stimulating factor (G-CSF), granulocytemacrophage colony stimulating factor (GM-CSF), follicle stimulating hormone (FSH), human chorionic gonadotrophin (hCG), luteinizing hormone (LH), an interferon, an interleukin, an antibody, or one or more sialylated fragments of said glycoproteins.

8. The process of claim 1, wherein at least one sialic acid precursor additive is selected from the group consisting of ManNAc, acetylated ManNAc, peracetylated ManNAc and fetuin.

9. The process of claim 1, wherein the glycoprotein is GM-CSF, the expression cell line is NM-F9 (deposited under the accession number DSM ACC2606), the sialic acid precursor additive is ManNAc, and the ManNac concentration determined in step b) and employed in step c) is 90 mM.

10. A process for the production of a highly active glycoprotein GM-CSF, comprising:
   (a) providing a human expression cell line which is NM-F9 (deposited under the accession number DSM ACC2606), and transfecting said cell line with a nucleic acid encoding the glycoprotein GM-CSF;
   (b) expressing said GM-CSF glycoprotein in said NM-F9 cell line in a medium supplemented with ManNAc at a concentration of 90 mM.

* * * * *

UNITED STATES PATENT AND TRADEMARK OFFICE
CERTIFICATE OF CORRECTION

PATENT NO. : 8,609,370 B2  
APPLICATION NO. : 10/589447  
DATED : December 17, 2013  
INVENTOR(S) : Goletz et al.

Page 1 of 1

It is certified that error appears in the above-identified patent and that said Letters Patent is hereby corrected as shown below:

In the specification

Column 29, line 19, "5g" -- should read -- 5 μg --.

Column 29, line 55, "ATG MT" -- should read -- ATG AAT --.

Column 29, line 57, "1.5 1" -- should read -- 1.5 μl --.

Column 29, line 58, "0.8-1.0 1" -- should read -- 0.8-1.0 μl --.

Column 29, line 58, "5 l of cDNA" -- should read -- 5 μl of cDNA --.

Column 29, line 59, "1.5 lof 2 mM" -- should read -- 1.5 μl of 2 mM --.

Column 29, line 59, "0.2 1 of Ampli-" -- should read -- 0.2 μl of Ampli- --.

Column 29, line 60, "0.2 1 of 0.25 M" -- should read -- 0.2 μl of 0.25 μM --.

Column 29, line 60, "0.7-0.8 1" -- should read -- 0.7-0.8 μl --.

Column 29, line 61, "50 M" -- should read -- 50 μM --.

Column 29, line 61, "15 1" -- should read -- 15 μl --.

Column 29, line 65, "0.2 1" -- should read -- 0.2 μl --.

Signed and Sealed this  
Eighth Day of December, 2015

Michelle K. Lee  
*Director of the United States Patent and Trademark Office*